US011198727B2

(12) United States Patent
Johnson et al.

(10) Patent No.: US 11,198,727 B2
(45) Date of Patent: Dec. 14, 2021

(54) METHODS AND SYSTEMS FOR PREDICTING RESPONSE TO ANTI-TNF THERAPIES

(71) Applicant: Scipher Medicine Corporation, Waltham, MA (US)

(72) Inventors: Keith J. Johnson, Wayland, MA (US); Susan Dina Ghiassian, Boston, MA (US)

(73) Assignee: SCIPHER MEDICINE CORPORATION, Waltham, MA (US)

( * ) Notice: Subject to any disclaimer, the term of this patent is extended or adjusted under 35 U.S.C. 154(b) by 0 days.

(21) Appl. No.: 16/394,046

(22) Filed: Apr. 25, 2019

(65) Prior Publication Data

US 2019/0284270 A1 Sep. 19, 2019

Related U.S. Application Data

(63) Continuation of application No. PCT/US2019/022588, filed on Mar. 15, 2019.

(60) Provisional application No. 62/644,070, filed on Mar. 16, 2018.

(51) Int. Cl.
| | |
|---|---|
| *C07K 16/24* | (2006.01) |
| *G16H 50/30* | (2018.01) |
| *A61P 19/02* | (2006.01) |
| *G16B 40/30* | (2019.01) |
| *G16B 45/00* | (2019.01) |
| *C12Q 1/6883* | (2018.01) |
| *C12Q 1/6827* | (2018.01) |
| *G16B 20/20* | (2019.01) |
| *C12Q 1/6851* | (2018.01) |

(52) U.S. Cl.
CPC .......... *C07K 16/241* (2013.01); *A61P 19/02* (2018.01); *C12Q 1/6827* (2013.01); *C12Q 1/6851* (2013.01); *C12Q 1/6883* (2013.01); *G16B 20/20* (2019.02); *G16B 40/30* (2019.02); *G16B 45/00* (2019.02); *G16H 50/30* (2018.01); *C12Q 2600/158* (2013.01); *G01N 2800/52* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 7,863,021 B2 | 1/2011 | Schrodi et al. | |
| 7,919,264 B2 | 4/2011 | Maksymowych et al. | |
| 7,935,482 B2 | 5/2011 | Bankaitis-Davis et al. | |
| 8,092,998 B2 | 1/2012 | Stuhlmuller et al. | |
| 9,086,418 B2 | 7/2015 | Maksymowych et al. | |
| 9,200,324 B2 | 12/2015 | Cavet et al. | |
| 9,387,246 B2 | 7/2016 | Graham | |
| 9,753,041 B2 | 9/2017 | Alman et al. | |
| 9,822,400 B2 | 11/2017 | Dennis, Jr. et al. | |
| 9,945,870 B2 | 4/2018 | Weiskopf et al. | |
| 10,018,637 B2 | 7/2018 | Schafer et al. | |
| 10,086,072 B2 | 10/2018 | Singh et al. | |
| 10,161,936 B2 | 12/2018 | Wagner | |
| 10,246,748 B2 | 4/2019 | Therianos et al. | |
| 10,301,679 B2 | 5/2019 | Schrodi et al. | |
| 10,324,088 B2 | 6/2019 | Singh et al. | |
| 10,385,398 B2 | 8/2019 | Hakonarson et al. | |
| 10,571,467 B2 | 2/2020 | Singh et al. | |
| 10,718,765 B2 | 7/2020 | Eastman et al. | |
| 2009/0221522 A1 | 9/2009 | Hidalgo et al. | |
| 2011/0059445 A1 | 3/2011 | Rutgeerts et al. | |
| 2011/0257893 A1 | 10/2011 | Taylor et al. | |
| 2012/0041683 A1 | 2/2012 | Vaske et al. | |
| 2012/0158391 A1 | 6/2012 | Vaske et al. | |
| 2013/0040835 A1 | 2/2013 | Harris | |
| 2015/0142465 A1 | 5/2015 | Vaske et al. | |
| 2016/0042119 A1 | 2/2016 | Lehrach et al. | |
| 2016/0110496 A1 | 4/2016 | Taylor et al. | |
| 2016/0146831 A1 | 5/2016 | Hueber et al. | |
| 2016/0162657 A1 | 6/2016 | Menche et al. | |
| 2016/0194709 A1 | 7/2016 | Nagy et al. | |
| 2016/0232279 A1 | 8/2016 | Ghiassian et al. | |
| 2017/0145501 A1 | 5/2017 | Folkersen | |
| 2018/0011966 A1 | 1/2018 | Vaske et al. | |
| 2018/0046751 A1 | 2/2018 | Vaske et al. | |
| 2018/0046752 A1 | 2/2018 | Vaske et al. | |
| 2019/0050523 A1 | 2/2019 | Ghiassian et al. | |
| 2019/0060449 A1 | 2/2019 | Singh et al. | |
| 2019/0080051 A1 | 3/2019 | Menche et al. | |

FOREIGN PATENT DOCUMENTS

| | | |
|---|---|---|
| WO | WO-2015/006213 A1 | 1/2015 |
| WO | WO-2015/084461 A2 | 6/2015 |
| WO | WO-2017/083564 A1 | 5/2017 |

(Continued)

OTHER PUBLICATIONS

Kim at al. in Korean Journal of Internal Medicine (2015) vol. 30:148-160.*
Xing et al. in PLoS Computational Biology (2011) vol. 7, No. 3:e-pp. 1-19.*
U.S. Appl. No. 16/277,216.
Abreu, M.T., Anti-TNF Failures in Crohn's Disease, Gastroenterol Hepatol (N.Y.), 7(1):37-39 (2011).
Barabási, A.L et al., Network medicine: a network-based approach to human disease, Nat. Rev. Genet, 12(1):56-68 (2011).
Cao, M. et al., Going the distance for protein function prediction: a new distance metric for protein interaction networks, PLOS One, 8(10): e76339 (2013), 12 pages.

(Continued)

*Primary Examiner* — Lori A. Clow
(74) *Attorney, Agent, or Firm* — Wilson Sonsini Goodrich & Rosati

(57) ABSTRACT

Methods and systems for administering anti-TNF therapy to subjects who have been determined to display a gene expression response signature established to distinguish between responsive and non-responsive prior subjects who have received the anti-TNF therapy.

11 Claims, 7 Drawing Sheets

(56) References Cited

FOREIGN PATENT DOCUMENTS

| WO | WO-2017/091777 A1 | 6/2017 |
| WO | WO-2017/093750 A1 | 6/2017 |
| WO | WO-2019/178546 A1 | 9/2019 |
| WO | WO-2020/264426 | 12/2020 |

OTHER PUBLICATIONS

Del Sol, A. et al., Diseases as network perturbations, Curr. Opin. Biotechnol., 21(4):566-571 (2010).

Ding, N.S. et al., Systematic review: predicting and optimizing response to anti-TNF therapy in Crohn's disease—algorithm for practical management, Aliment Pharmacol. Ther., 43(1):30-51 (2016).

Eisenberg, E. and Levanon, E.Y., Human housekeeping genes, revisited, Trends in Genetics, 29(10):569-574 (2013).

Goodman, S.N., et al., What does research reproducibility mean?, Sci. Transl. Med., 8(341):341-353 (2016).

Hall, K.T. et al.,. Genetics and the placebo effect: the placebome, Trends Mol. Med., 21(5):285-294 (2015).

Han, J-D. J. et al, Evidence for dynamically organized modularity in the yeast protein-protein interaction network, Nature, 430: 88-93 (2004).

Hanauer, S. B. et al, Maintenance Infliximab for Crohn's disease: the ACCENT I randomized trial, Lancet, 359:1541-1549 (2002).

Ioannidis, J.P., et al., Replication validity of genetic association studies, Nat. Genet. 29:(3)306-309 (2001).

Ioannidis, J.P.A., Why most published research findings are false, PLoS Med. 2(8):e124 (2005), pp. 0697-0701.

Johnson, W. E. and Li, C., Adjusting batch effects in microarray expression data using empirical Bayes methods, Biostatistics 8(1), 118-127 (2007).

Menche, J. et al, Uncovering disease-disease relationships through the incomplete interactome, Science, 347(6224):1257601 (2015), 10 pages.

Nakamura, S. et al., Identification of baseline gene expression signatures predicting therapeutic responses to three biologic agents in rheumatoid arthritis: a retrospective observational study, Arthritis Research & Therapy, 18:159 (2016), 12 pages.

Roda, G. et al., Loss of Response to Anti-TNFs: Definition, Epidemiology, and Management, Clin. Gastroentorl., 7:e135 (2016), 5 pages.

Sands, B.E. et al., Infliximab maintenance therapy for fistulizing Crohn's disease, N. Engl. J. Med., 350:876-885 (2004)).

Santolini, M., A personalized, multiomics approach identifies genes involved in cardiac hypertrophy and heart failure, Systems Biology and Applications, 4:12 (2018), 13 pages.

Specht, D. F., Probabilistic Neural Networks, Neural Networks, 3(1):109-118 (1990).

Thomson, T. M. et al., Blood-based identification of non-responders to anti-TNF therapy in rheumatoid arthritis, BMC Med Genomics, 8:26 (2015), 12 pages.

Toonen, E. J. et al., Validation Study of Existing Gene Expression Signatures for Anti-TNF Treatment in Patients with Rheumatoid Arthritis, PLOS ONE 7(3): e33199, 6 pages.

Wachi, S. et al, Interactome-transcriptome analysis reveals the high centrality of genes differentially expressed in lung cancer tissues, Bioinformatics, 21(23): 4205-8 (2005).

Winthrop, K. L. et al, The unmet need in rheumatology: Reports from the targeted therapies meeting 2017, Clin. Immunol., 186: 87-93 (2018).

De Souza et al. The IBD Interactome: an Integrated View of Aetiology, Pathogenesis and Therapy, Nature Reviews Gastroenterology & Hepatology, 14(12): 739-749 (2017).

International Search Report for PCT/US2019/022588 (Methods and Systems for Predicting Response to Anti-TNF Therapies, filed Mar. 15, 2019), issued by ISA/US, 4 pages (dated May 28, 2019).

Putrik et al. Variations in Criteria Regulating Treatment with Reimbursed Biologic DMARDs Across European Countries. Are Differences Related to Country's Wealth?, Ann Rheum Dis, 73(11):2010-2021 (2014).

Written Opinion for PCT/US2019/022588 (Methods and Systems for Predicting Response to Anti-TNF Therapies, filed Mar. 15, 2019), issued by ISA/US, 18 pages (dated May 28, 2019).

You, S. et al, A Systems Approach to Rheumatoid Arthritis, PLOS ONE, 7(12): e51508 (2012), pp. 1-11.

Bienkowska, J. R. et al., Convergent random forest predictor: Methodology for predicting drug response from genome-scale data applied to anti-TNF response, Genomics 94:423-432 (2009).

Julia, A. et al., An Eight-Gene Blood Expression Profile Predicts the Response to Infliximab in Rheumatoid Arthritis, PLOS One, 4(10):1-10 (2009).

Thompson, T. M. et al., Blood-based identification of non-responders to anti-TNF therapy in rheumatoid arthritis, BMC Medical Genomics, 8:26 (2015), 12 pages.

International Search Report for PCT/US2020/39991, 5 pages (dated Nov. 24, 2020).

Written Opinion for PCT/US2020/39991, 13 pages (dated Nov. 24, 2020).

Arijs et al., Mucosal gene signatures to predict response to infliximab in patients with ulcerative colitis. Gut 58: 1612-1619 (2009).

\* cited by examiner

METHODS AND SYSTEMS FOR PREDICTING RESPONSE TO ANTI-TNF THERAPIES

CROSS-REFERENCE TO RELATED APPLICATIONS

The present application is a continuation of PCT Application No. PCT/US2019/022588, filed Mar. 15, 2019, which claims priority to U.S. Provisional Application No. 62/644,070, filed Mar. 16, 2018, each of which is incorporated herein by reference.

BACKGROUND

Tumor necrosis factor (TNF) is a cell signaling protein related to regulation of immune cells and apoptosis, and is implicated in a variety of immune and autoimmune-mediated disorders. In particular, TNF is known to promote inflammatory response, which causes many problems associated with autoimmune disorders, such as rheumatoid arthritis, psoriatic arthritis, ankylosing spondylitis, Crohn's disease, ulcerative colitis, inflammatory bowel disease, chronic psoriasis, hidradenitis suppurativa, asthma, and juvenile idiopathic arthritis.

TNF-mediated disorders are currently treated by inhibition of TNF, and in particular by administration of an anti-TNF agent (i.e., by anti-TNF therapy). Examples of anti-TNF agents approved in the United States include monoclonal antibodies that target TNF, such as adalimumab (Humira®), certolizumab pegol (Cimiza®), golimumab (Simponi® and Simponi Aria®), and infliximab (Remicade®), decoy circulating receptor fusion proteins such as etanercept (Enbrel®), and biosimilars, such as adalimumab ABP 501 (AMGEVITA™), and etanercept biosimilars GP2015 (Erelzi).

SUMMARY

A significant known problem with anti-TNF therapies is that response rates are inconsistent. Indeed, recent international conferences designed to bring together leading scientists and clinicians in the fields of immunology and rheumatology to identify unmet needs in these fields almost universally identify uncertainty in response rates as an ongoing challenge. For example, the 19$^{th}$ annual International Targeted Therapies meeting, which held break-out sessions relating to challenges in treatment of a variety of diseases, including rheumatoid arthritis, psoriatic arthritis, axial spondyloarthritis, systemic lupus erythematous, and connective tissue diseases (e.g. Sjogren's syndrome, Systemic sclerosis, vasculitis including Bechet's and IgG4 related disease), identified certain issues common to all of these diseases, specifically, "the need for better understanding the heterogeneity within each disease . . . so that predictive tools for therapeutic responses can be developed. See Winthrop, et al., "The unmet need in rheumatology: Reports from the targeted therapies meeting 2017," *Clin. Immunol.* pii: S1521-6616(17)30543-0, Aug. 12, 2017. Similarly, extensive literature relating to treatment of Crohn's Disease with anti-TNF therapy consistently bemoans erratic response rates and inability to predict which patients will benefit. See, e.g., M. T. Abreu, "Anti-TNF Failures in Crohn's Disease," *Gastroenterol Hepatol (N.Y.)*, 7(1):37-39 (January 2011); see also Ding et al., "Systematic review: predicting and optimising response to anti-TNF therapy in Crohn's disease—algorithm for practical management," *Aliment Pharmacol. Ther.*, 43(1):30-51 (January 2016) (reporting that "[p]rimary nonresponse to anti-TNF treatment affects 13-40% of patients.").

Thus, a significant number of patients to whom anti-TNF therapy is currently being administered do not benefit from the treatment, and could even be harmed. Known risks of serious infection and malignancy associated with anti-TNF therapy are so significant that product approvals typically require so-called "black box warnings" be included on the label. Other potential side effects of such therapy include, for example, congestive heart failure, demyelinating disease, and other systemic side effects. Furthermore, given that several weeks to months of treatment are required before a patient is identified as not responding to anti-TNF therapy (i.e., is a non-responder to anti-TNF therapy), proper treatment of such patients can be significantly delayed as a result of the current inability to identify responder vs non-responder subjects. See, e.g., Roda et al., "Loss of Response to Anti-TNFs: Definition, Epidemiology, and Management," *Clin. Trani. Gastroenterol.*, 7(1):e135 (January 2016) (citing Hanauer et al., "ACCENT I Study group. Maintenance Infliximab for Crohn's disease: the ACCENT I randomized trial," *Lancet* 59:1541-1549 (2002); Sands et al., "Infliximab maintenance therapy for fistulizing Crohn's disease," *N Engl. J. Med.* 350:876-885 (2004)).

Taken together, particularly given that these anti-TNF therapies can be quite expensive (typically costing upwards of $40,000-60,000 per patient per year), these challenges make clear that technologies capable of defining, identifying, and/or characterizing responder vs. non-responder patient populations would represent a significant technological advance, and would provide significant value to patients and to the healthcare industry more broadly, including to doctors, regulatory agencies, and drug developers. The present disclosure provides such technologies.

Provided technologies, among other things, permit care providers to distinguish subjects likely to benefit from anti-TNF therapy from those who are not, reduce risks to patients, increase timing and quality of care for non-responder patient populations, increase efficiency of drug development, and avoid costs associated with administering ineffective therapy to non-responder patients or with treating side effects such patients experience upon receiving anti-TNF therapy.

Provided technologies embody and/or arise from, among other things, certain insights that include, for example, identification of the source of a problem with certain conventional approaches to defining responder vs. non-responder populations and/or that represent particularly useful strategies for defining classifiers that distinguish between such populations. For example, as described herein, the present disclosure identifies that one source of a problem with many conventional strategies for defining responder vs. non-responder populations through consideration of gene expression differences in the populations is that they typically prioritize or otherwise focus on highest fold changes; the present disclosure teaches that such an approach misses subtle but meaningful differences relevant to disease biology. Moreover, the present disclosure offers an insight that mapping of genes with altered expression levels onto a human interactome map (in particular onto a human interactome map that represents experimentally supported physical interactions between cellular components which, in some embodiments, explicitly excludes any theoretical, calculated, or other interaction that has been proposed but not experimentally validated), can provide a useful and effective classifier for defining responders vs. non-responders to anti-TNF therapy. In some embodiments, genes included in such a classifier represent a connected module on the human interactome.

Accordingly, in some embodiments, the present disclosure provides a method of treating subjects with anti-TNF therapy, the method comprising a step of: administering the anti-TNF therapy to subjects who have been determined to display a gene expression response signature established to distinguish between responsive and non-responsive prior subjects who have received the anti-TNF therapy.

In some embodiments, the present disclosure provides, in a method of administering anti-TNF therapy, the improvement that comprises administering the therapy selectively to subjects who have been determined to display a gene expression response signature established to distinguish between responsive and non-responsive prior subjects who have received the anti-TNF therapy.

In some embodiments, the present disclosure provides a kit comprising a gene expression response signature established to distinguish between responsive and non-responsive prior subjects who have received anti-TNF therapy.

In some embodiments, the present disclosure provides a method of determining a gene expression response signature, the method comprising steps of: mapping genes whose expression levels significantly correlate to clinical responsiveness or non-responsiveness of anti-TNF therapy to a human interactome map; and selecting a plurality of genes determined to cluster with one another in a human interactome map, thereby establishing the gene expression response signature.

In some embodiments, the present disclosure provides a method of determining a gene expression response signature, the method comprising steps of: mapping genes whose expression levels significantly correlate to clinical responsiveness or non-responsiveness of anti-TNF therapy to a human interactome map; and selecting a plurality of genes associated with response to anti-TNF therapy and characterized by their topological properties when mapped on a human interactome map (e.g., genes that are proximal or otherwise close together in space on a human interactome map), thereby establishing the gene expression response signature.

In some embodiments, the present disclosure provides a method of determining a gene expression response signature, the method comprising steps of: mapping genes whose expression levels significantly correlate to clinical responsiveness or non-responsiveness of anti-TNF therapy to a human interactome map; and selecting a plurality of genes selected by diffusion state distance with one another in a human interactome map, thereby establishing the gene expression response signature.

Definitions

Administration: As used herein, the term "administration" typically refers to the administration of a composition to a subject or system, for example to achieve delivery of an agent that is, or is included in or otherwise delivered by, the composition.

Agent: As used herein, the term "agent" refers to an entity (e.g., for example, a lipid, metal, nucleic acid, polypeptide, polysaccharide, small molecule, etc., or complex, combination, mixture or system [e.g., cell, tissue, organism] thereof), or phenomenon (e.g., heat, electric current or field, magnetic force or field, etc.).

Amino acid: As used herein, the term "amino acid" refers to any compound and/or substance that can be incorporated into a polypeptide chain, e.g., through formation of one or more peptide bonds. In some embodiments, an amino acid has the general structure $H_2N—C(H)(R)—COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. As used herein, the term "standard amino acid" refers to any of the twenty L-amino acids commonly found in naturally occurring peptides. "Nonstandard amino acid" refers to any amino acid, other than the standard amino acids, regardless of whether it is or can be found in a natural source. In some embodiments, an amino acid, including a carboxy- and/or amino-terminal amino acid in a polypeptide, can contain a structural modification as compared to the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared to the general structure. In some embodiments, such modification may, for example, alter the stability or the circulating half-life of a polypeptide containing the modified amino acid as compared to one containing an otherwise identical unmodified amino acid. In some embodiments, such modification does not significantly alter a relevant activity of a polypeptide containing the modified amino acid, as compared to one containing an otherwise identical unmodified amino acid. As will be clear from context, in some embodiments, the term "amino acid" may be used to refer to a free amino acid; in some embodiments it may be used to refer to an amino acid residue of a polypeptide, e.g., an amino acid residue within a polypeptide.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Antagonist: As used herein, the term "antagonist" may refer to an agent, or condition whose presence, level, degree, type, or form is associated with a decreased level or activity of a target. An antagonist may include an agent of any chemical class including, for example, small molecules, polypeptides, nucleic acids, carbohydrates, lipids, metals, and/or any other entity that shows the relevant inhibitory activity. In some embodiments, an antagonist may be a "direct antagonist" in that it binds directly to its target; in some embodiments, an antagonist may be an "indirect antagonist" in that it exerts its influence by means other than binding directly to its target; e.g., by interacting with a regulator of the target, so that the level or activity of the target is altered). In some embodiments, an "antagonist" may be referred to as an "inhibitor".

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., polyethylene glycol, etc.]).

Associated: Two events or entities are "associated" with one another, as that term is used herein, if the presence, level, degree, type and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Combination Therapy: As used herein, the term "combination therapy" refers to a clinical intervention in which a subject is simultaneously exposed to two or more therapeutic regimens (e.g. two or more therapeutic agents). In some embodiments, the two or more therapeutic regimens may be administered simultaneously. In some embodiments, the two or more therapeutic regimens may be administered sequentially (e.g., a first regimen administered prior to administration of any doses of a second regimen). In some embodiments, the two or more therapeutic regimens are administered in overlapping dosing regimens. In some embodiments, administration of combination therapy may involve administration of one or more therapeutic agents or modalities to a subject receiving the other agent(s) or modality. In some embodiments, combination therapy does not necessarily require that individual agents be administered together in a single composition (or even necessarily at the same time). In some embodiments, two or more therapeutic agents or modalities of a combination therapy are administered to a subject separately, e.g., in separate compositions, via separate administration routes (e.g., one agent orally and another agent intravenously), and/or at different time points. In some embodiments, two or more therapeutic agents may be administered together in a combination composition, or even in a combination compound (e.g., as part of a single chemical complex or covalent entity), via the same administration route, and/or at the same time.

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Corresponding to: As used herein, the phrase "corresponding to" refers to a relationship between two entities, events, or phenomena that share sufficient features to be reasonably comparable such that "corresponding" attributes are apparent. For example, in some embodiments, the term may be used in reference to a compound or composition, to designate the position and/or identity of a structural element in the compound or composition through comparison with an appropriate reference compound or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids. For example, those skilled in the art will be aware of various sequence alignment strategies, including software programs such as, for example, BLAST®, CS-BLAST®, CUSASW++, DIAMOND, FASTA™, GGSEARCH/GL SEARCH, Genoogle, HMMER™, HHpred/HHsearch, IDF, Infernal, KLAST, USEARCH, parasail, PSI-BLAST®, PSI-Search, ScalaBLAST®, Sequilab, SAM, SSEARCH, SWAPHI, SWAPHI-LS, SWIMM, or SWIPE that can be utilized, for example, to identify "corresponding" residues in polypeptides and/or nucleic acids in accordance with the present disclosure.

Dosing regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Improved, increased or reduced: As used herein, the terms "improved," "increased," or "reduced,", or grammatically comparable comparative terms thereof, indicate values that are relative to a comparable reference measurement. For example, in some embodiments, an assessed value achieved with an agent of interest may be "improved" relative to that obtained with a comparable reference agent. Alternatively or additionally, in some embodiments, an assessed value achieved in a subject or system of interest may be "improved" relative to that obtained in the same subject or system under different conditions (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc.).

Pharmaceutical composition: As used herein, the term "pharmaceutical composition" refers to an active agent, formulated together with one or more pharmaceutically acceptable carriers. In some embodiments, the active agent is present in unit dose amounts appropriate for administration in a therapeutic regimen to a relevant subject (e.g., in amounts that have been demonstrated to show a statistically significant probability of achieving a predetermined therapeutic effect when administered), or in a different, comparable subject (e.g., in a comparable subject or system that differs from the subject or system of interest in presence of one or more indicators of a particular disease, disorder or condition of interest, or in prior exposure to a condition or agent, etc.). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Primary Non-Responder: As used herein, the term "primary non-responder" refers to a subject that displays a lack of improvement in clinical signs and symptoms after receiving anti-TNF therapy for a period of time. Those skilled in the art will understand that the medical community may establish an appropriate period of time for any particular disease or condition, or for any particular patient or patient type. To give but a few examples, in some embodiments, the period of time may be at least 8 weeks. In some embodiments, the period of time may be at least 12 weeks. In some embodiments, the period of time may be 14 weeks.

Reference: As used herein, the term "reference" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Secondary Non-Responder: As used herein, the term "secondary non-responder" refers to a subject that displays an initial improvement in clinical signs or symptoms after receiving anti-TNF therapy, but show a statistically significant decrease in such improvement over time.

Therapeutically effective amount: As used herein, the term "therapeutically effective amount" refers to an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder and/or condition. In some embodiments, a therapeutically effective amount is administered in a single dose; in some embodiments, multiple unit doses are required to deliver a therapeutically effective amount.

Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature.

BRIEF DESCRIPTION OF THE DRAWING

FIG. 2A is a receiver operating characteristic (ROC) curve and FIG. 2B illustrates the Negative Predictive Value (NPV) vs. True Negative Rate (TNR) curve. The classifier is able to detect 70% of the non-responders with 100% accuracy, and 100% of the non-responders with 90% accuracy.

FIG. 3A is an ROC curve and FIG. 3B illustrates the NPV vs. TNR curve. The classifier is able to detect 50% of the non-responders with 100% accuracy.

DETAILED DESCRIPTION OF CERTAIN EMBODIMENTS

Figure 1A:
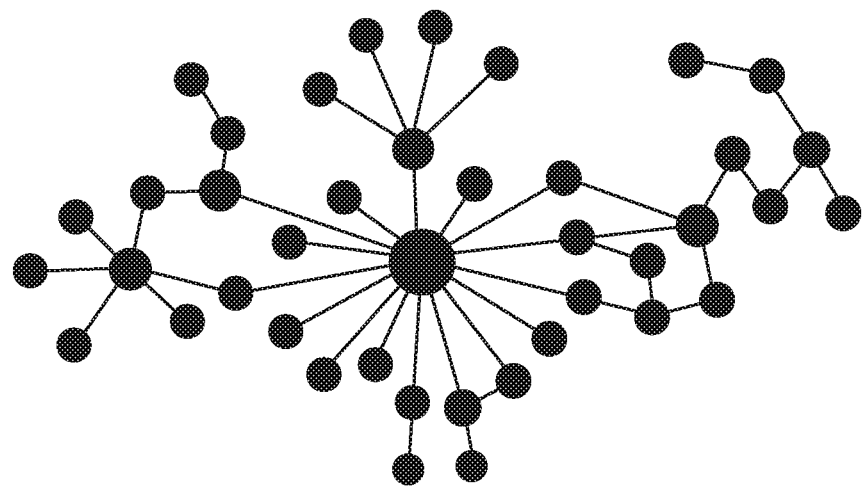
FIGS. 1A and 1B are plots illustrating ulcerative colitis (UC) response signature genes modules detected using the human interactome (HI) from the UC cohort. The response signature genes found in gene expression data form a significant cluster when mapped to the HI (FIG. 1A) and is much larger than expected by chance (FIG. 1B) which reflects an underlying biology of response.

As noted, the response rate for patients undergoing anti-TNF therapy is inconsistent. Technologies that reliably identify responsive or non-responsive subjects would be beneficial, as they would avoid wasteful and even potentially damaging administration of therapy to subjects who will not respond, and furthermore would allow timely determination of more appropriate treatment for such subjects. The present disclosure provides such technologies, addressing needs of patients, their families, drug developers, and medical professionals each of whom suffers under the current system.

While significant effort has been invested in efforts to develop technologies that reliably predict responsiveness (e.g., by identifying responsive vs. non-responsive populations) or development of resistance for certain therapeutic agents, regimens, or modalities, success has been elusive, and almost exclusively limited to the oncology sector. Complex disorders, such as autoimmune and/or cardiovascular diseases have proven to be particularly challenging.

Cancer is typically associated with particular strong driver genes, which dramatically simplifies the analysis required to identify responder vs non-responder patient populations, and significantly improves success rates. By contrast, diseases associated with more complex genetic (and/or epigenetic) contributions, have thus far presented an insurmountable challenge for available technologies.

Indeed, a large number of published reports describe efforts to develop technologies for predicting responsiveness to anti-TNF therapy in inflammatory conditions (e.g., rheumatoid arthritis), most commonly relying on blood-based gene expression classifiers. See, e.g., Nakamura et al. "Identification of baseline gene expression signatures predicting therapeutic responses to three biologic agents in rheumatoid arthritis: a retrospective observational study" *Arthritis Research & Therapy* (2016) 18:159 DOI 10.1186/s13075-016-1052-8. However, a clinically utilizable classifier has not yet been identified. Notably, Toonen et al. performed an independent study that tested eight different gene expression signatures predicting response to anti-TNF, and reported that most signatures failed to demonstrate sufficient predictive value to be of utility. See M. Toonen et al., "Validation Study of Existing Gene Expression Signatures for Anti-TNF Treatment in Patients with Rheumatoid Arthritis," *PLOS ONE* 7(3): e33199. Thomson et al. attempted to describe a blood-based classifier to identify non-responders to one anti-TNF therapy, infliximab, in rheumatoid arthritis. Thomson et al., "Blood-based identification of non-responders to anti-TNF therapy in rheumatoid arthritis," *BMC Med Genomics*, 8:26, *1-12 (2015). Their proposed classifier comprised 18 signaling mechanisms indicative of higher TNF-mediated inflammatory signaling in responders at baseline, versus higher levels of specific metabolic activities in non-responders at baseline. The test, however, did not reach the level of predictive accuracy required for commercialization and so development was stopped.

Typically, conventional strategies for defining responder vs. non-responder classifiers for anti-TNF therapy rely on machine-learning approaches, using mean values across classes of response, and focusing on genes with the highest fold changes, often in a pathway-based context. The present disclosure identifies various sources of problems with these conventional approaches, and, moreover, provides technologies that solve or avoid the problems, thereby satisfying the long felt need within the community for accurate and/or useful predictive classifiers.

Among other things, the present disclosure appreciates that machine learning may be useful for finding correlation between datasets of patients, but fails to achieve sufficient predictive accuracy across cohorts. Furthermore, the present disclosure identifies that prioritizing or otherwise focusing on highest fold changes misses subtle but meaningful differences relevant to disease biology. Still further, the present disclosure offers an insight that mapping of genes with altered expression levels onto a human interactome (e.g., that represents experimentally supported physical interactions between cellular components and, in some embodiments, explicitly excludes any theoretical, calculated, or other interaction that has been proposed but not experimentally validated) can provide a useful and effective classifier for defining responders vs. non-responders to anti-TNF therapy. In some embodiments, genes included in such a classifier represent a connected module in the human interactome.

Anti-TNF Therapy

TNF-mediated disorders are currently treated by inhibition of TNF, and in particular by administration of an anti-TNF agent (i.e., by anti-TNF therapy). Examples of anti-TNF agents approved for use in the United States include monoclonal antibodies such as adalimumab (Humira®), certolizumab pegol (Cimiza®), infliximab (Remicade®), and decoy circulating receptor fusion proteins such as etanercept (Enbrel®). These agents are currently approved for use in treatment of indications, according to dosing regimens, as set forth below in Table 1:

TABLE 1

| Indication | Adalimumab[1] | Certolizumab Pegol[1] | Infliximab[2] | Etanercept[1] | Golimumab[1] | Golimumab[2] |
|---|---|---|---|---|---|---|
| Juvenile Idiopathic Arthritis | 10 kg (22 lbs) to <15 kg (33 lbs): 10 mg every other week<br>15 kg (33 lbs) to <30 kg (66 lbs): 20 mg every other week<br>≥30 kg (66 lbs): 40 mg every other week | N/A | N/A | 0.8 mg/kg weekly, with a maximum of 50 mg per week | N/A | N/A |
| Psoriatic Arthritis | 40 mg every other week | 400 mg initially and at week 2 and 4, followed by 200 mg every other week; for maintenance dosing, 400 mg every 4 weeks | 5 mg/kg at 0, 2 and 6 weeks, then every 8 weeks | 50 mg once weekly with or without methotrexate | 50 mg administered by subcutaneous injection once a month | N/A |
| Rheumatoid Arthritis | 40 mg every other week | 400 mg initially and at Weeks 2 and 4, followed by 200 mg every other week; for maintenance dosing, 400 mg every 4 weeks | In conjunction with methotrexate, 3 mg/kg at 0, 2 and 6 weeks, then every 8 weeks | 50 mg once weekly with or without methotrexate | 50 mg once a month | 2 mg/kg intravenous infusion over 30 minutes at weeks 0 and 4, then every 8 weeks |
| Ankylosing Spondylitis | 40 mg every other week | 400 mg (given as 2 subcutaneous injections of 200 mg each) initially and at weeks 2 and 4, followed by 200 mg every other week or 400 mg every 4 weeks | 5 mg/kg at 0, 2 and 6 weeks, then every 6 weeks | 50 mg once weekly | 50 mg administered by subcutaneous injection once a month | N/A |
| Adult Crohn's Disease | Initial dose (Day 1): 160 mg<br>Second dose two weeks later (Day 15): 80 mg<br>Two weeks later (Day 29): Begin a maintenance dose of 40 mg every other week | 400 mg initially and at Weeks 2 and 4<br>Continue with 400 mg every four weeks | 5 mg/kg at 0, 2 and 6 weeks, then every 8 weeks. | N/A | N/A | N/A |
| Pediatric Crohn's Disease | 17 kg (37 lbs) to <40 kg (88 lbs): Initial dose (Day 1): 80 mg<br>Second dose two weeks later (Day 15): 40 mg<br>Two weeks later (Day 29): Begin a maintenance dose of 20 mg every other week ≥40 kg (88 lbs): Initial dose (Day 1): 160 mg | N/A | 5 mg/kg at 0, 2 and 6 weeks, then every 8 weeks. | N/A | N/A | N/A |

TABLE 1-continued

| Indication | Adalimumab[1] | Certolizumab Pegol[1] | Infliximab[2] | Etanercept[1] | Golimumab[1] | Golimumab[2] |
|---|---|---|---|---|---|---|
| | Second dose two weeks later (Day 15): 80 mg Two weeks later (Day 29): Begin a maintenance dose of 40 mg every other week | | | | | |
| Ulcerative Colitis | Initial dose (Day 1): 160 mg Second dose two weeks later (Day 15): 80 mg Two weeks later (Day 29): Begin a maintenance dose of 40 mg every other week | N/A | 5 mg/kg at 0, 2 and 6 weeks, then every 8 weeks. | N/A | N/A | N/A |
| Plaque Psoriasis | 80 mg initial dose; 40 mg every other week beginning one week after initial dose | N/A | N/A | 50 mg twice weekly for 3 months, followed by 50 mg once weekly | N/A | N/A |
| Hidradenitis Suppurativa | Initial dose (Day 1): 160 mg Second dose two weeks later (Day 15): 80 mg Third dose (Day 29) and subsequent doses: 40 mg every week | N/A | N/A | N/A | N/A | N/A |
| Uveitis | 80 mg initial dose; 40 mg every other week beginning one week after initial dose | N/A | N/A | N/A | N/A | N/A |

[1]Administered by subcutaneous injection.
[2]Administered by intravenous infusion.

The present disclosure provides technologies relevant to anti-TNF therapy, including those therapeutic regimens as set forth in Table 1. In some embodiments, the anti-TNF therapy is or comprises administration of infliximab (Remicade®), adalimumab (Humira®), certolizumab pegol (Cimiza®), etanercept (Enbel®), or biosimilars thereof. In some embodiments, the anti-TNF therapy is or comprises administration of infliximab (Remicade®) or adalimumab (Humira®). In some embodiments, the anti-TNF therapy is or comprises administration of infliximab (Remicade®). In some embodiments, the anti-TNF therapy is or comprises administration of adalimumab (Humira®).

In some embodiments, the anti-TNF therapy is or comprises administration of a biosimilar anti-TNF agent. In some embodiments, the anti-TNF agent is selected from infliximab biosimilars such as CT-P13, BOW015, SB2, Inflectra, Renflexis, and Ixifi, adalimumab biosimilars such as ABP 501 (AMGEVITA™), Adfrar, and Hulio™ and etanercept biosimilars such as HD203, SB4 (Benepali®), GP2015, Erelzi, and Intacept.

In some embodiments, the present disclosure defines patient populations to whom anti-TNF therapy should (or should not) be administered. In some embodiments, technologies provided by the present disclosure generate information useful to doctors, pharmaceutical companies, payers, and/or regulatory agencies who wish to ensure that anti-TNF therapy is administered to responder populations and/or is not administered to non-responder populations.

Diseases, Disorders or Conditions

In general, provided disclosures are useful in any context in which administration of anti-TNF therapy is contemplated or implemented. In some embodiments, provided technologies are useful in the diagnosis and/or treatment of subjects suffering from a disease, disorder, or condition associated with aberrant (e.g., elevated) TNF expression and/or activity. In some embodiments, provided technologies are useful in monitoring subjects who are receiving or have received anti-TNF therapy. In some embodiments, provided technologies identify whether a subject will or will not respond to a given anti-TNF therapy. In some embodiments, the provided technologies identify whether a subject will develop resistance to a given anti-TNF therapy.

Accordingly, the present disclosure provides technologies relevant to treatment of the various disorders related to TNF, including those listed in Table 1. In some embodiments, a subject is suffering from a disease, disorder, or condition selected from rheumatoid arthritis, psoriatic arthritis, ankylosing spondylitis, Crohn's disease (adult or pediatric), ulcerative colitis, inflammatory bowel disease, chronic psoriasis, plaque psoriasis, hidradenitis suppurativa, asthma, uveitis, and juvenile idiopathic arthritis. In some embodiments, the disease, disorder, or condition is rheumatoid arthritis. In some embodiments, the disease, disorder, or condition is psoriatic arthritis. In some embodiments, the disease, disorder, or condition is ankylosing spondylitis. In some embodiments, the disease, disorder, or condition is Crohn's disease. In some embodiments, the disease, disorder, or condition is adult Crohn's disease. In some embodiments, the disease, disorder, or condition is pediatric Crohn's disease. In some embodiments, the disease, disorder, or condition is inflammatory bowel disease. In some embodiments, the disease, disorder, or condition is ulcerative colitis. In some embodiments, the disease, disorder, or condition is chronic psoriasis. In some embodiments, the disease, disorder, or condition is plaque psoriasis. In some embodiments, the disease, disorder, or condition is hidradenitis suppurativa. In some embodiments, the disease, disorder, or condition is asthma. In some embodiments, the disease, disorder, or condition is uveitis. In some embodiments, the disease, disorder, or condition is juvenile idiopathic arthritis.

Provided Classifier(s)

The present disclosure provides gene expression response signatures that serve as gene classifiers and identify (i.e., predict) which patients will or will not respond to anti-TNF therapy. That is, the present disclosure provides methods of determining gene expression response signatures that are characteristic of anti-TNF responder or non-responder populations. In some embodiments, a particular gene expression response signature classifies responder or non-responder populations for a particular anti-TNF therapy (e.g., a particular anti-TNF agent and/or regimen). In some embodiments, responder and/or non-responder populations for different anti-TNF therapies (e.g., different anti-TNF agents and/or regimens) may overlap or be co-extensive; in some such embodiments, the present disclosure may provide gene expression response signatures that serve as gene classifiers for responder and/or non-responder populations across anti-TNF therapies.

In some embodiments, as described herein, a gene expression response signature is identified by retrospective analysis of gene expression levels in biological samples from patients who have received anti-TNF therapy and have been determined to respond (i.e., are responders) or not to respond (i.e., are non-responders). In some embodiments, all such patients have received the same anti-TNF therapy (optionally for the same or different periods of time); alternatively or additionally, in some embodiments, all such patients have been diagnosed with the same disease, disorder or condition. In some embodiments, patients whose biological samples are analyzed in the retrospective analysis had received different anti-TNF therapy (e.g., with a different anti-TNF agent and/or according to a different regimen); alternatively or additionally, in some embodiments, patients whose biological samples are analyzed in the retrospective analysis have been diagnosed with different diseases, disorders, or conditions.

Typically, a gene expression response signature as described herein is determined by comparison of gene expression levels in the responder vs. non-responder populations whose biological samples are analyzed in a retrospective analysis as described herein. Genes whose expression levels show statistically significant differences between the responder and non-responder populations may be included in the gene response signature.

In some embodiments, the present disclosure embodies an insight that the source of a problem with certain prior efforts to identify or provide gene expression response signatures through comparison of gene expression levels in responder vs non-responder populations have emphasized and/or focused on (often solely on) genes that show the largest difference (e.g., greater than 2-fold change) in expression levels between the populations. The present disclosure appreciates that even genes those expression level differences are relatively small (e.g., less than 2-fold change in expression) provide useful information and are valuably included in a gene expression response signature in embodiments described herein.

Moreover, in some embodiments, the present disclosure embodies an insight that analysis of interaction patterns of genes whose expression levels show statistically significant differences (optionally including small differences) between responder and non-responder populations as described herein provides new and valuable information that materially improves the quality and predictive power of a gene expression response signature.

Further, as noted, the present disclosure provides technologies that allow practitioners to reliably and consistently predict response in a cohort of subjects. In particular, for example, the rate of response for some anti-TNF therapies is less than 35% within a given cohort of subjects. The provided technologies allow for prediction of greater than 65% accuracy within a cohort of subjects a response rate (i.e., whether certain subjects will or will not respond to a given therapy). In some embodiments, the methods and systems described herein predict 65% or greater the subjects that are responders (i.e., will respond to anti-TNF therapy) within a given cohort. In some embodiments, the methods and systems described herein predict 70% or greater the subjects that are responders within a given cohort. In some embodiments, the methods and systems described herein predict 80% or greater the subjects that are responders within a given cohort. In some embodiments, the methods and systems described herein predict 90% or greater the subjects that are responders within a given cohort. In some embodiments, the methods and systems described herein predict 100% the subjects that are responders within a given cohort. In some embodiments, the methods and systems described herein predict 65% or greater the subjects that are non-responders (i.e., will not respond to anti-TNF therapy) within a given cohort. In some embodiments, the methods and systems described herein predict 70% or greater the subjects that are non-responders within a given cohort. In some embodiments, the methods and systems described herein predict 80% or greater the subjects that are non-responders within a given cohort. In some embodiments, the methods and systems described herein predict 90% or greater the subjects that are non-responders within a given cohort. In some embodiments, the methods and systems described herein predict 100% of the subjects that are non-responders within a given cohort.

Defining Classifier(s)

A provided gene expression response signature (i.e., a gene classifier) is a gene or set of genes that can be used to determine whether a subject will or will not respond to a particular therapy (e.g., anti-TNF therapy). In some embodiments, a gene expression response signature can be identified using mRNA and/or protein expression datasets, for example as may be or have been prepared from validated biological data (e.g., biological data derived from publicly available databases such as Gene Expression Omnibus ("GEO")). In some embodiments, a gene expression response signature may be derived by comparing gene expression levels of known responsive and known non-responsive prior subjects to a specific therapy (e.g., anti-TNF therapy). In some embodiments, certain genes (i.e., signature genes) are selected from this cohort of gene expression data to be used in developing the gene expression response signature.

In some embodiments, signature genes are identified by methods analogous to those reported by Santolini, "A personalized, multiomics approach identifies genes involved in cardiac hypertrophy and heart failure," Systems Biology and Applications, (2018)4:12; doi:10.1038/s41540-018-0046-3, which is incorporated herein by reference. In some embodiments, signature genes are identified by comparing gene expression levels of known responsive and non-responsive prior subjects and identifying significant changes between the two groups, wherein the significant changes can be large differences in expression (e.g., greater than 2-fold change), small differences in expression (e.g., less than 2-fold change), or both. In some embodiments, genes are ranked by significance of difference in expression. In some embodiments, significance is measured by Pearson correlation between gene expression and response outcome. In some embodiments, signature genes are selected from the ranking by significance of difference in expression. In some embodiments, the number of signature genes selected is less than the total number of genes analyzed. In some embodiments, 200 signature genes or less are selected. In some embodiments 100 genes or less are selected.

In some embodiments, signature genes are selected in conjunction with their location on a human interactome (HI), a map of protein-protein interactions. Use of the HI in this way encompasses a recognition that mRNA activity is dynamic and determines the actual over and under expression of proteins critical to understanding certain diseases. In some embodiments, genes associated with response to certain therapies (i.e., anti-TNF therapy) may cluster (i.e., form a cluster of genes) in discrete modules on the HI map. The existence of such clusters is associated with the existence of fundamental underlying disease biology. In some embodiments, a gene expression response signature is derived from signature genes selected from the cluster of genes on the HI map. Accordingly, in some embodiments, a gene expression response signature is derived from a cluster of genes associated with response to anti-TNF therapy on a human interactome map.

In some embodiments, genes associated with response to certain therapies exhibit certain topological properties when mapped onto a human interactome map. For example, in some embodiments, a plurality of genes associated with response to anti-TNF therapy and characterized by their position (i.e., topological properties, e.g., their proximity to one another) on a human interactome map.

In some embodiments, genes associated with response to certain therapies (i.e., anti-TNF therapy) may exist within close proximity to one another on the HI map. Said proximal genes, do not necessarily need to share fundamental underlying disease biology. That is, in some embodiments, proximal genes do not share significant protein interaction. Accordingly, in some embodiments, the gene expression response signature is derived from genes that are proximal on a human interactome map. In some embodiments, the gene expression response signature is derived from certain other topological features on a human interactome map.

In some embodiments, genes associated with response to certain therapies (i.e., anti-TNF therapy) may be determined by Diffusion State Distance (DSD) (see Cao, et al., *PLOS One*, 8(10): e76339 (Oct. 23, 2013)) when used in combination with the HI map.

In some embodiments, signature genes are selected by (1) ranking genes based on the significance of difference of expression of genes as compared to known responders and known non-responders; (2) selecting genes from the ranked genes and mapping the selected genes onto a human interactome map; and (3) selecting signature genes from the genes mapped onto the human interactome map.

In some embodiments, signature genes (e.g., selected from the Santolini method, or using various network topological properties including, but not limited to, clustering, proximity and diffusion-based methods) are provided to a probabilistic neural network to thereby provide (i.e., "train") the gene expression response signature. In some embodiments, the probabilistic neural network implements the algorithm proposed by D. F. Specht in "Probabilistic Neural Networks," *Neural Networks*, 3(1):109-118 (1990), which is incorporated herein by reference. In some embodiments, the probabilistic neural network is written in the R-statistical language, and knowing a set of observations described by a vector of quantitative variables, classifies observations into a given number of groups (e.g., responders and non-responders). The algorithm is trained with the data set of signature genes taken from known responders and non-responders and guesses new observations that are provided. In some embodiments, the probabilistic neural network is one derived from CRAN.R-project.org.

Alternatively or additionally, in some embodiments, a gene expression response signature can be trained in the probabilistic neural network using a cohort of known responders and non-responders using leave-one-out cross and/or k-fold cross validation. In some embodiments, such a process leaves one sample out (i.e., leave-one-out) of the analysis and trains the classifier only based on the remaining samples. In some embodiments, the updated classifier is then used to predict a probability of response for the sample that's left out. In some embodiments, such a process can be repeated iteratively, for example, until all samples have been left out once. In some embodiments, such a process randomly partitions a cohort of known responders and non-responders into k equal sizes groups. Of the k groups, a single group is retained as validation data for testing the model, and the remaining groups are used as training data. Such a process can be repeated k times, with each of the k groups being used exactly once as the validation data. In some embodiments, the outcome is a probability score for each sample in the training set. Such probability scores can correlate with actual response outcome. A Recursive Operating Curves (ROC) can be used to estimate the performance of the classifier. In some embodiments, an Area Under Curve (AUC) of about 0.6 or higher reflects a suitable validated classifier. In some embodiments, a Negative Predictive Value (NPV) of 0.9 reflects a suitable validated classifier. In some embodiments, a classifier can be tested in a completely independent (i.e., blinded) cohort to, for example, confirm the suitability (i.e., using leave-one-out and/or k-fold cross validation). Accordingly, in some embodiments, provided methods further comprise one or more steps of validating a gene expression response signature, for example, by assigning probability of response to a group of known responders and non-responders; and checking the gene expression response signature against a blinded group of responders and non-responders. The output of these processes is a trained gene expression response signature useful for establishing whether a subject will or will not respond to a particular therapy (e.g., anti-TNF therapy).

Accordingly, in some embodiments, the gene expression response signature is established to distinguish between responsive and non-responsive prior subjects who have received a type of therapy, e.g., anti-TNF therapy. This gene expression response signature, derived from these prior responders and non-responders, is used to classify subjects (outside of the previously-identify cohorts) as responders or non-responders, i.e., can predict whether a subject will or will not respond to a given therapy. In some embodiments, the response and non-responsive prior subjects suffered from the same disease, disorder, or condition.

Detecting Classifier(s)

Detecting gene classifiers in subjects, once the gene classifier is identified, is a routine matter for those of skill in the art. In other words, by first defining the gene classifier, a variety of methods can be used to determine whether a subject or group of subjects express the established gene classifier. For example, in some embodiments, a practitioner can obtain a blood or tissue sample from the subject prior to administering of therapy, and extract and analyze mRNA profiles from said blood or tissue sample. The analysis of mRNA profiles can be performed by any method known to those of skill in the art, including, but not limited gene arrays, RNA-sequencing, nanostring sequencing, real-time quantitative reverse transcription PCR (qRT-PCR), bead arrays, or enzyme-linked immunosorbent assay (ELISA). Accordingly, in some embodiments, the present disclosure provides methods of determining whether a subject is classified as a responder or non-responder, comprising measuring gene expression by at least one of a microarray, RNA sequencing, real-time quantitative reverse transcription PCR (qRT-PCR), bead array, and ELISA. In some embodiments, the present disclosure provides methods of determining whether a subject is classified as a responder or non-responder comprising measuring gene expression of a subject by RNA sequencing (i.e., RNAseq).

In some embodiments, the provided technologies provide methods comprising determining, prior to administering anti-TNF therapy, that a subject displays a gene expression response signature associated with response to anti-TNF therapy; and administering the anti-TNF therapy to the subject determined to display the gene expression response signature. In some embodiments, the provided technologies provide methods comprising determining, prior to administering anti-TNF therapy, that a subject does not display the gene expression response signature; and administering a therapy alternative to anti-TNF therapy to the subject determine not to display the gene expression signature.

In some embodiments, the therapy alternative to anti-TNF therapy is selected from rituximab (Rituxan®), sarilumab (Kevzare®), tofacitinib citrate (Xeljanz®), leflunomide (Arava®), vedolizumab (Entyvio®), tocilizumab (Actemra®), anakinra (Kineret®), and abatacept (Orencia®).

In some embodiments, gene expression is measured by subtracting background data, correcting for batch effects, and dividing by mean expression of housekeeping genes. See Eisenberg & Levanon, "Human housekeeping genes, revisited," *Trends in Genetics*, 29(10):569-574 (October 2013). In the context of microarray data analysis, background subtraction refers to subtracting the average fluorescent signal arising from probe features on a chip not complimentary to any mRNA sequence, i.e. signals that arise from non-specific binding, from the fluorescence signal intensity of each probe feature. The background subtraction can be performed with different software packages, such as Affymetrix™ Gene Expression Console. Housekeeping genes are involved in basic cell maintenance and, therefore, are expected to maintain constant expression levels in all cells and conditions. The expression level of genes of interest, i.e., those in the response signature, can be normalized by dividing the expression level by the average expression level across a group of selected housekeeping genes. This housekeeping gene normalization procedure calibrates the gene expression level for experimental variability. Further, normalization methods such as robust multi-array average ("RMA") correct for variability across different batches of microarrays, are available in R packages recommended by either Illumina™ and/or Affymetrix™ platforms. The normalized data is log transformed, and probes with low detection rates across samples are removed. Furthermore, probes with no available genes symbol or Entrez ID are removed from the analysis.

In some embodiments, the present disclosure provides a kit comprising a gene expression response signature established to distinguish between responsive and non-responsive prior subjects who have received anti-TNF therapy. In some embodiments, the kit compares levels of gene expression of a subject to the gene expression response signature (i.e., the gene classifier) established to distinguish between responsive and non-responsive prior subjects who have received anti-TNF therapy.

Using Classifiers

Patient Stratification

Among other things, the present disclosure provides technologies for predicting responsiveness to anti-TNF therapies. In some embodiments, provided technologies exhibit consistency and/or accuracy across cohorts superior to previous methodologies.

Thus, the present disclosure provides technologies for patient stratification, defining and/or distinguishing between responder and non-responder populations. For example, in some embodiments, the present disclosure provides methods for treating subjects with anti-TNF therapy, which methods, in some embodiments, comprise a step of: administering the anti-TNF therapy to subjects who have been determined to display a gene expression response signature established to distinguish between responsive and non-responsive prior subjects who have received the anti-TNF therapy. In some such embodiments, the gene expression response signature includes a plurality of genes established to distinguish between responsive and non-responsive prior subjects for a given anti-TNF therapy. In some embodiments, the plurality of genes are determined to cluster with one another in a human interactome map. In some embodiments, the plurality of genes are proximal in a human interactome map. In some embodiments, the plurality of genes comprise genes that are shown to be statistically significantly different between responsive and non-responsive prior subjects.

Therapy Monitoring

Further, the present disclosure provides technologies for monitoring therapy for a given subject or cohort of subjects. As a subject's gene expression level can change over time, it may, in some instances, be necessary or desirable to evaluate a subject at one or more points in time, for example, at specified and or periodic intervals.

In some embodiments, repeated monitoring under time permits or achieves detection of one or more changes in a subject's gene expression profile or characteristics that may impact ongoing treatment regimens. In some embodiments, a change is detected in response to which particular therapy administered to the subject is continued, is altered, or is suspended. In some embodiments, therapy may be altered, for example, by increasing or decreasing frequency and/or amount of administration of one or more agents or treatments with which the subject is already being treated. Alternatively or additionally, in some embodiments, therapy may be altered by addition of therapy with one or more new agents or treatments. In some embodiments, therapy may be altered by suspension or cessation of one or more particular agents or treatments.

To give but one example, if a subject is initially classified as responsive (because the subject's gene expression correlated to a gene expression response signature associated with a disease, disorder, or condition), a given anti-TNF therapy can then be administered. At a given interval (e.g., every six months, every year, etc.), the subject can be tested again to ensure that they still qualify as "responsive" to a given anti-TNF therapy. In the event the gene expression levels for a given subject change over time, and the subject no longer expresses genes associated with the gene expression response signature, or now expresses genes associated with non-responsiveness, the subject's therapy can be altered to suit the change in gene expression.

Accordingly, in some embodiments, the present disclosure provides methods of administering therapy to a subject previously determined to display a gene expression response signature associated with anti-TNF therapy, wherein the subject displays a gene expression response signature associated with response to anti-TNF therapy.

In some embodiments, the present disclosure provides methods of treating subjects with anti-TNF therapy, the method comprising a step of: administering the anti-TNF therapy to subjects who have been determined to display a gene expression response signature established to distinguish between responsive and non-responsive prior subjects who have received the anti-TNF therapy.

In some embodiments, the present disclosure provides methods further comprising determining, prior to the administering, that a subject displays the gene expression response signature; and administering the anti-TNF therapy to the subject determined to display the gene expression response signature.

In some embodiments, the present disclosure provides methods further comprising determining, prior to the administering, that a subject does not display the gene expression response signature; and administering a therapy alternative to anti-TNF therapy to the subject determined not to display the gene expression response signature.

In some embodiments, the gene expression response signature was established to distinguish between responsive and non-responsive prior subjects who have received the anti-TNF therapy by a method comprising steps of: mapping genes whose expression levels significantly correlate to clinical responsiveness or non-responsiveness to a human interactome map; and selecting a plurality of genes determined to cluster with one another in a human interactome map, thereby establishing the gene expression response signature.

In some embodiments, the gene expression response signature was established to distinguish between responsive and non-responsive prior subjects who have received the anti-TNF therapy by a method comprising steps of: mapping genes whose expression levels significantly correlate to clinical responsiveness or non-responsiveness to a human interactome map; and selecting a plurality of genes determined to be proximal with one another in a human interactome map, thereby establishing the gene expression response signature.

In some embodiments, the present disclosure provides methods further comprising steps of: validating the gene expression response signature by assigning probability of response to a group of known responders and non-responders; and checking the gene expression response signature against a blinded group of responders and non-responders.

In some embodiments, the responsive and non-responsive prior subjects suffered from the same disease, disorder, or condition.

In some embodiments, the subjects to whom the anti-TNF therapy is administered are suffering from the same disease, disorder or condition as the prior responsive and non-responsive prior subjects.

In some embodiments, the gene expression response signature includes expression levels of a plurality of genes derived from a cluster of genes associated with response to anti-TNF therapy on a human interactome map.

In some embodiments, the gene expression response signature includes expression levels of a plurality of genes proximal to genes associated with response to anti-TNF therapy on a human interactome map.

In some embodiments, the gene expression response signature includes expression levels of a plurality of genes determined to cluster with one another in a human interactome map.

In some embodiments, the gene expression response signature includes expression levels of a plurality of genes that are proximal in a human interactome map.

In some embodiments, genes of the subject are measured by at least one of a microarray, RNA sequencing, real-time quantitative reverse transcription PCR (qRT-PCR), bead array, ELISA, and protein expression.

In some embodiments, the subject suffers from a disease, disorder, or condition selected from rheumatoid arthritis, psoriatic arthritis, ankylosing spondylitis, Crohn's disease, ulcerative colitis, chronic psoriasis, hidradenitis suppurativa, and juvenile idiopathic arthritis.

In some embodiments, the anti-TNF therapy is or comprises administration of infliximab, adalimumab, etanercept, cirtolizumab pegol, goliluma, or biosimilars thereof. In some embodiments, the anti-TNF therapy is or comprises administration of infliximab or adalimumab.

In some embodiments, the present disclosure provides, in a method of administering anti-TNF therapy, the improvement that comprises administering the therapy selectively to subjects who have been determined to display a gene expression response signature established to distinguish between responsive and non-responsive prior subjects who have received the anti-TNF therapy.

In some embodiments, the responsive and non-responsive prior subjects suffered from the same disease, disorder, or condition.

In some embodiments, the subjects to whom the anti-TNF therapy is administered are suffering from the same disease, disorder or condition as the prior responsive and non-responsive prior subjects.

In some embodiments, the gene expression response signature includes expression levels of a plurality of genes derived from a cluster of genes associated with response to anti-TNF therapy on a human interactome map.

In some embodiments, the anti-TNF therapy is or comprises administration of infliximab, adalimumab, etanercept, cirtolizumab pegol, goliluma, or biosimilars thereof.

In some embodiments, the disease, disorder, or condition is selected from rheumatoid arthritis, psoriatic arthritis, ankylosing spondylitis, Crohn's disease, ulcerative colitis, chronic psoriasis, hidradenitis suppurativa, and juvenile idiopathic arthritis.

In some embodiments, the disease, disorder, or condition is rheumatoid arthritis.

In some embodiments, the disease, disorder, or condition is ulcerative colitis.

In some embodiments, the present disclosure provides use of an anti-TNF therapy in the treatment of a subject determined to display a gene expression response signature established to distinguish between responsive and non-responsive prior subjects who have received the anti-TNF therapy.

In some embodiments, prior to use of the anti-TNF therapy, determining that the subject displays the gene expression response signature. In some embodiments, prior to use of the anti-TNF therapy, determining that the subject does not display the gene expression response signature.

In some embodiments, the gene expression response signature was established to distinguish between responsive and non-responsive prior subjects who have received the anti-TNF therapy by a method comprising steps of: mapping genes whose expression levels significantly correlate to clinical responsiveness or non-responsiveness to a human interactome map; and selecting a plurality of genes determined to cluster with one another in a human interactome map, thereby establishing the gene expression response signature.

In some embodiments, the gene expression response signature was established to distinguish between responsive and non-responsive prior subjects who have received the anti-TNF therapy by a method comprising steps of: mapping genes whose expression levels significantly correlate to clinical responsiveness or non-responsiveness to a human interactome map; and selecting a plurality of genes determined to be proximal with one another in a human interactome map, thereby establishing the gene expression response signature.

In some embodiments, the gene expression response signature was established to distinguish between responsive and non-responsive prior subjects who have received the anti-TNF therapy by the method further comprising steps of validating the gene expression response signature by assigning probability of response to a group of known responders and non-responders; and checking the gene expression response signature against a blinded group of responders and non-responders.

Therapy Reimbursement

Provided technologies also provide significant value to regulatory agencies and payers (i.e., insurance companies). As noted, in some embodiments, provided technologies provide consistent and reliable means for predicting anti-TNF therapy response for a given subject or cohort of subjects. As also noted, for some anti-TNF therapies, response rate of subjects is only about 65%. With a 35% chance that a given anti-TNF therapy may have no or sub-optimal impact, or indeed a negative impact on a subject, it is clearly beneficial for regulatory agencies and payers to be able to reliably predict when a subject will or will not respond to a given therapy.

Generally, when a patient is prescribed a particular medication or therapy, the patient obtains or receives the medication or therapy from a care provider, such as a pharmacy or a medical practitioner. Commonly, the pharmacy or medical practitioner pays for the medication outright, and then will either pass the cost on to the patient (if coverage from an insurance company/payer is not available), or will seek reimbursement for the medication from the insurance company payer. If the medication is covered, the payer reimburses the pharmacy or medical practitioner, and the patient either pays nothing, or a co-pay. This system operates under the assumption that the medication will be beneficial to the patient. But, failure of a patient to respond to a given therapy results in considerable wasted expense (not to mention wasted time on the part of the patient), coupled with a chance that the patient's disease, disorder, or condition could progress, or that the patient may be subject to a side effect associated with a given anti-TNF therapy. Either scenario results in additional costs to the payer, as the payer has already reimbursed the pharmacy or medical practitioner for the therapy. These costs, however, could have been avoided in the first instance with proper analysis of the patient prior to administering the drug. Accordingly, the present disclosure provides technologies for reimbursement of medical expenses relating to anti-TNF therapy.

Whether a payer will cover a given therapy is determined by a committee referred to as the "Pharmacy and Therapeutics Committee" (the "P&T Committee"). The P&T Committee is responsible for managing the "formulary" of the agency. The formulary is a continually updated list of medications and related information, and includes a list of medications and medication-associated products or devices, medication use policies, important ancillary drug information, decision support tools, and organization guidelines for an agency or a payer. The P&T Committee, continually reviewing and revising the formulary, establishes policies regarding the use of drugs, therapies, and drug-related products, and identifies those that are most medically appropriate and cost-effective. Part of the review of the formulary is the pharmacoeconomic assessment, which includes cost-minimization to the patient and payer, but also consideration of nonmedication-related costs and financial consequences of the pharmacy and the organization as a whole. Therefore, relevant to the instant disclosure, it is the job of the P&T Committee to determine whether certain diagnostic methods should be required or associated with a particular medication. By requiring that a subject obtain certain diagnostic information prior to administration of a particular therapy, the payer can ensure that the subject will indeed respond, and that no costs are wasted reimbursing a subject for therapy that did not work.

Accordingly, the P&T Committee can require that either prior authorization or step therapy be required before dispensing specific medications. Prior authorization requires the prescriber (i.e., the physician) to receive pre-approval for prescribing a particular medication in order for that medication to qualify for coverage. Drugs that require prior authorization will not be approved for payment until the conditions for approval of the drug are met. Prior authorization is useful because it can address the need to obtain additional clinical patient information. Examples of such information include clinical diagnosis, height, weight, laboratory results, previous medications, and non-drug therapies related to a specific disease, disorder, or condition. Within the instant disclosure, a payer can require a prescriber receive prior authorization for administering particular anti-TNF therapies. For example, the payer can require that the patient prove that they have the particular gene expression associated with the gene expression response signature described herein (i.e., is a responder) prior to authorizing payment of a particular anti-TNF therapy. The payer can also deny coverage of a particular anti-TNF therapy if the patient is classified as a non-responder (i.e., does not express genes associated with the gene expression response signature). Requiring such prior authorization allows payers to avoid loss by reimbursing (covering) particular medications that may not be therapeutically effective for a given subject.

Further, similar to prior authorization, some payers may require that patients undergo step therapy prior to administering a particular drug. Step therapy is the requirement that a patient undergo a particular, approved, treatment prior to authorization of the requested drug. For example, for patients suffering from arthritis, a payer may require that a patient undergo therapy with non-steroidal anti-inflammatory drugs (NSAIDs) prior to administration of a different medication. Similarly, for example, a payer can require that a patient be classified as a responder or a non-responder based on the gene expression response signatures described generally herein. For example, if a patient is classified as a "non-responder" to a given anti-TNF therapy, the payer can require that the patient undergo alternative therapy prior to covering the given anti-TNF therapy. Utilizing this strategy allows for the payer to ensure that other venues of treatment are attempted before taking on the risk of paying for medication that is unlikely to have any effect for a given patient.

Accordingly, in some embodiments, the present disclosure provides technologies for reimbursement of medical expenses related to anti-TNF therapy. In some embodiments, the present disclosure provides technologies for adjudicating and reimbursing a care provider for anti-TNF therapy, such methods comprising: receiving a transaction from the care provider requesting reimbursement for the anti-TNF therapy; aggregating data for the anti-TNF therapy from a formulary; determining whether satisfying prior authorization conditions is required for the anti-TNF therapy; determining an amount of reimbursement using data aggregated from the formulary and whether the prior authorization conditions are satisfied.

In some embodiments, the formulary requires the prior authorization conditions are satisfied. In some embodiments, the prior authorization conditions comprise determining whether a subject displays a gene expression response signature established to distinguish between responsive and non-responsive prior subjects who have received the anti-TNF therapy.

In some embodiments, the subject satisfies the prior authorization conditions by expressing the gene expression response signature. In some embodiments, the care provider is reimbursed in an amount between 1% and 100% of the cost of the anti-TNF therapy.

In some embodiments, the subject does not satisfy the prior authorization conditions by not expressing the gene expression response signature. In some embodiments, the amount of reimbursement is 0%.

In some embodiments, the present disclosure provides a method of reimbursing medical expenses associated with administration of anti-TNF therapy to a subject, the method comprising: providing reimbursement if the subject had been determined to display a gene expression response signature established to distinguish between responsive and non-responsive prior subjects who have received the anti-TNF therapy; and not providing reimbursement if the subject had not been determined to display the gene expression response signature.

EXEMPLIFICATION

Examples below demonstrate gene expression response signatures (otherwise referred to as "classifiers" below) characteristic of subjects who do or do not respond to anti-TNF therapy.

Example 1: Determining Responder and Non-Responder Patient Populations—Ulcerative Colitis In accordance with the present disclosure, gene expression data from subjects diagnosed with ulcerative colitis (UC) who had received anti-TNF therapy was used to determine patients who are responders and non-responders to anti-TNF therapy. This UC cohort (GSE12251) included 23 patients diagnosed with UC, 11 of which did not respond to anti-TNF-therapy. The gene expression data for this cohort were generated using the Affymetrix™ platform.

The gene expression data was analyzed define a set of genes (response signature genes) whose expression patterns distinguish responders and non-responders. To do this, genes with significant gene expression deviations between responders and non-responders were relied on. Unlike conventional differential expression methods that look for high fold changes in gene expression between two groups, the present disclosure provides the insight that small but significant changes between two groups of patients should be included. The present disclosure thus identifies the source of a problem with conventional differential expression technologies.

Without wishing to be bound by any particular theory, the present disclosure provides an insight that small but significant differences impact responsiveness to therapy. Indeed, the present disclosure notes that, given that patients in these cohorts are all diagnosed with the same disease, they often may not manifest big FCs across genes. The present disclosure demonstrates that even very small but significant changes in gene expression will lead to a different treatment outcome.

Additionally, the present disclosure demonstrates that analysis of genes displaying small (but significant) expression differences, in context of a human "interactome" map, defines signatures that reliably distinguish responders from non-responders.

In-Cohort Analysis

Using a human interactome ("HI") map of gene connectivity that reveals features of underlying biology of response and is useful for understanding response signature genes.

Figure 1B:
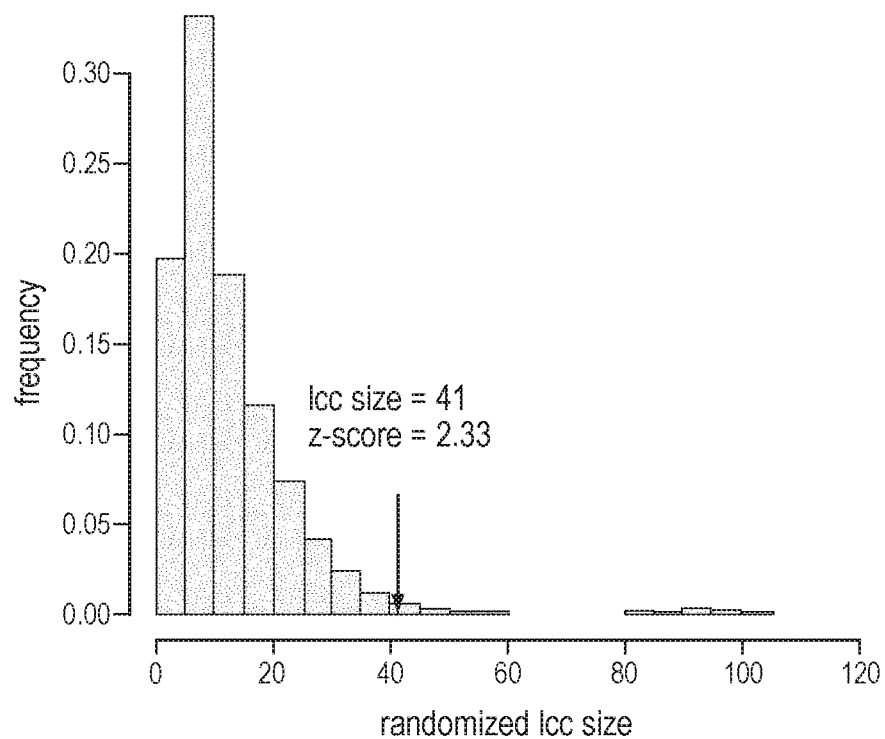

The top 200 genes (as measured by p-value from lowest to highest) whose expression values across patients were significantly correlated to clinical outcome after treatment were selected and mapped to HI. It was observed that even though these genes have been found using the gene expression data only, they form a significant cluster (module) on the HI, with the large connected component ("LCC," i.e., classifier genes) being much bigger that what is expected by chance HI (FIGS. 1A and 1B). Existence of such significant modules (z-score >1.6) has been repeatedly shown to be associated with underlying disease biology. See Barabási, et al., "Network medicine: a network-based approach to human disease," *Nat. Rev. Genet*, 12(1):56-68 (January 2011); Hall et al, "Genetics and the placebo effect: the placebome," *Trends Mol. Med.*, 21(5):285-294 (May 2015); del Sol, et al., "Diseases as network perturbations," *Curr. Opin. Biotechnol.*, 21(4):566-571 (August 2010).

FIGS. 1A and 1B show the subnetwork containing the genes correlated to phenotypic outcome in UC cohort as well as their interactions. A significant number of genes found by gene expression analysis form the LCC of the subgraph. The LCC genes (classifier genes) were then utilized to feed and train a probabilistic neural network. The result of the analysis shows a near perfect classifier with an Area Under the Curve (AUC) of 0.98 and with 100% accuracy in predicting non-responders.

Figure 2A:
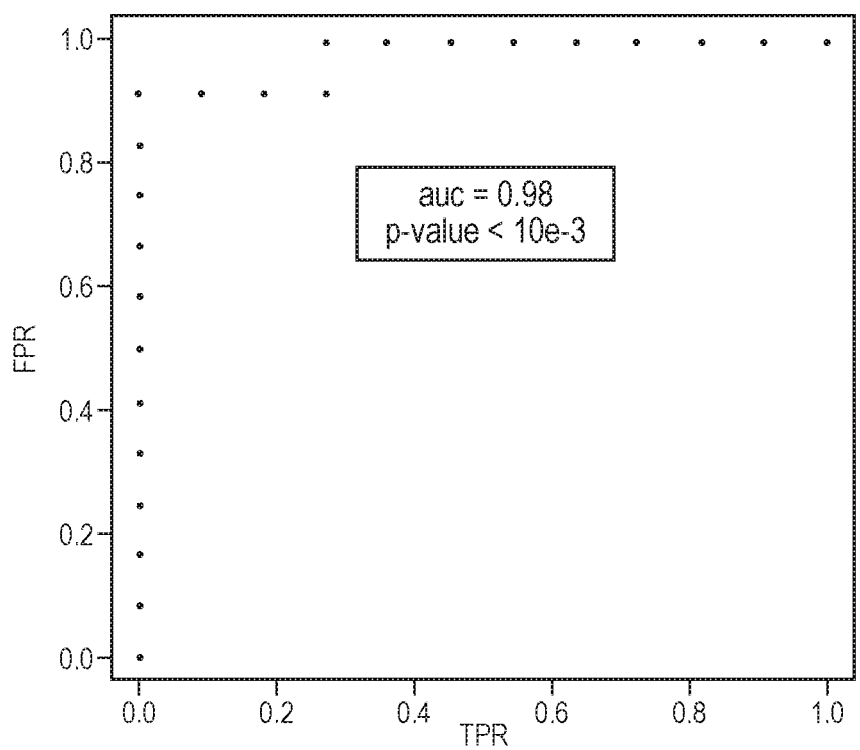
FIGS. 2A and 2B are plots illustrating in-cohort performance of response predictions of a near perfect classifier using leave-one-out cross-validation.
Figure 2B:
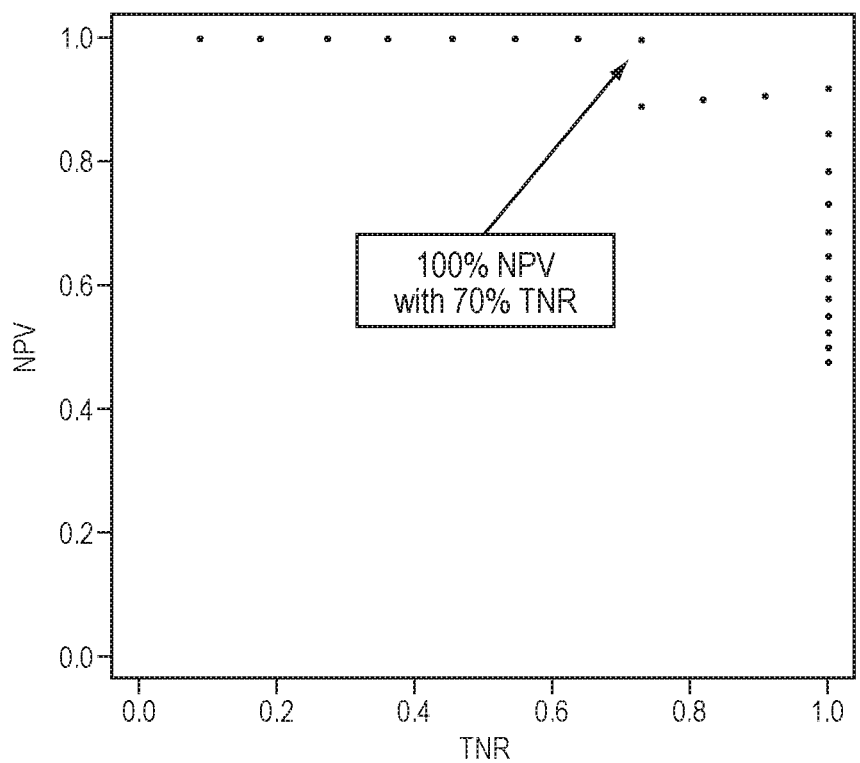

The performance of trained classifiers was validated using a leave-one-out cross validation approach. FIGS. 2A and 2B show the receiver operator curves (ROC) as well as negative prediction power (predicting non-responders) of the classifier. The classifier is able to detect 70% of the non-responders within a cohort.

TABLE 2

| Cohort ID | No. Genes Selected | No. Genes in HI | LCC Size | Significance |
|---|---|---|---|---|
| GSE12251 | 200 | 193 | 41 | 2.33 |

Table 2 represents the number and topological properties (i.e., the size of the largest component on the network and its significance) of response signature genes when mapped onto the network.

A known and major drawback of traditional gene expression analysis is the inability to reproduce the results across different studies. See Ioannidis J. P. A., "Why most published research findings are false," *PLoS Med.* 2(8):e124 (2005); Goodman S. N., et al., "What does research reproducibility mean?" *Sci. Transl. Med.*, 8(341):341-353 (2016); Ioannidis J. P., et al. "Replication validity of genetic association studies." *Nat. Genet.* 29: (3)306-309 (November 2001). Below, it is shown that the methods and systems described herein are able to make high accuracy predictions across cohorts. To estimate the power of the classifier, the classifier is tested in a completely independent cohort (GSE14580) and in a blinded fashion. The independent UC cohort includes 16 non-responders and 8 responders.

Figure 3A:
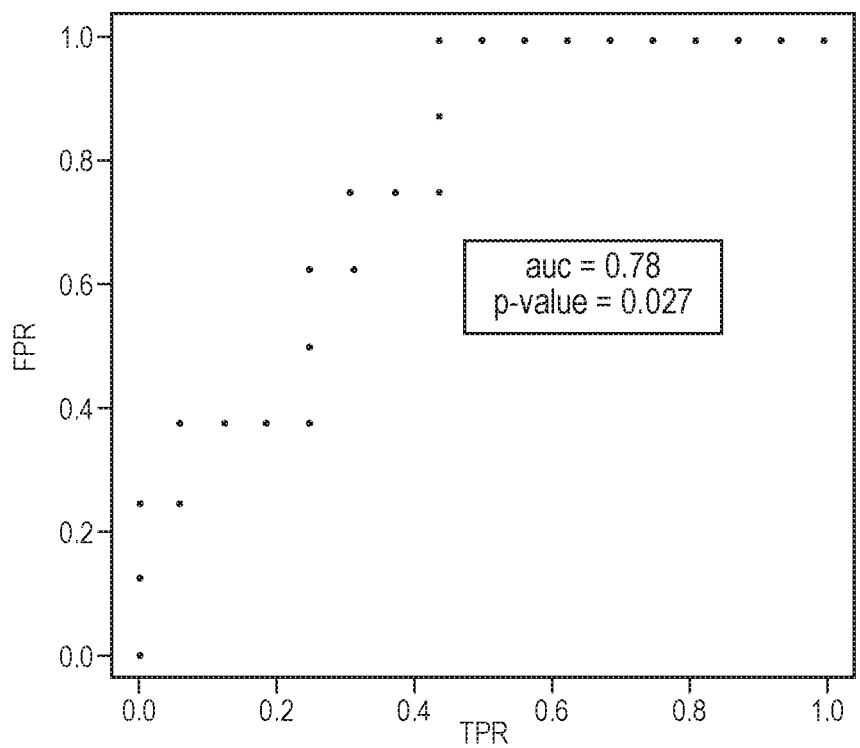
FIGS. 3A and 3B are plots illustrating cross-cohort performance of response prediction classifier when testing on an independent cohort.
Figure 3B:
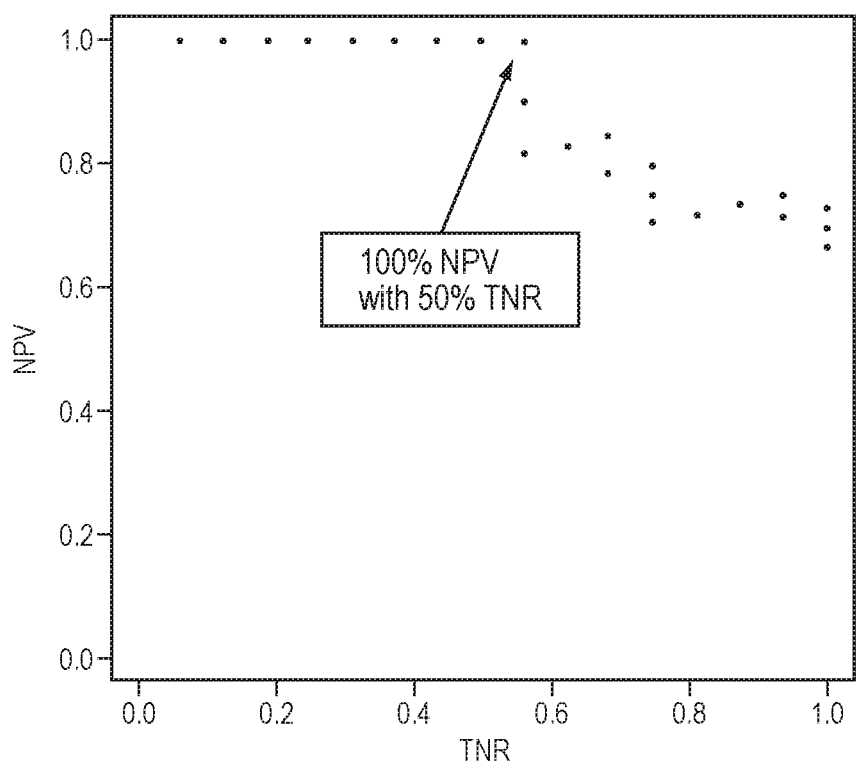

For cross-platform validation, the two cohorts were merged and batch effects removed using the R package, ComBat, a tool used for batch-adjusting gene expression data. See Johnson W. E., et al., "Adjusting batch effects in microarray expression data using empirical Bayes methods," *Biostatistics* 8(1), 118-127 (2007). The performance of the designed classifier was tested in the independent cohort (leave-one-batch-out cross validation). FIGS. 3A and 3B show the ROC and negative prediction curves associated with cross-cohort performance of the designed classifier. The trained classifier shows significantly high performance in the independent cohort with AUC of 0.78.

Aside from the high cross-cohort performance assessed by AUC, cross-cohort NPV (Negative Predictive Value) and TNR (True Negative Rate), which indicates the accuracy of detecting non-responders in a blind cohort, were also estimated (FIG. 3B). The cross-cohort validation shows that the classifier is able to predict at least 50% of non-responders (NPV=1, TNR=0.5). The classifier is able to detect more non-responders (TNR>0.5), which results in slight drop in NPV (FIG. 3B). Nevertheless, regardless of the selected point on the curve, the classifier meets or exceeds the commercial criteria (NPV of 0.9 and TNR of 0.5) set by health insurance companies.

Disease Biology of Non-Responders

The network defined by the analysis described herein provides insights into underlying biology of this response prediction. The classifier genes within the response module were analyzed using GO terms to identify the most highly enriched pathways. We found that inflammatory signaling pathways (including TNF signaling) were highly enriched, as were pathways linked to sumoylation, ubiquitination, proteasome function, proteolytic degradation and antigen presentation in immune cells. Thus, the network approach described herein has captured protein interactions for selecting genes within the response module that clearly reflect the biology of the disease and drug response at the independent patient level and allow the accurate prediction of response to anti-TNF therapies from a baseline sample.

Discussion

A known and significant problem with existing anti-TNF therapy approaches is that "many patients do not respond to the . . . therapy (primary non-response—PNR), or lose response during the treatment (secondary loss of response—LOR)." See, e.g., Roda et al., *Clin Gastroentorl.* 7:e135, January 2016. Specifically, reports indicate that "around 10-30% of patients do not respond to the initial treatment and 23-46% of patients lose response over time" Id. Thus, overall, the drug response rate for anti-TNF therapy (and in particular for anti-TNF therapy to treat UC patients) is below 65%, resulting in continued disease progression and escalating treatment costs for the majority of the patient population. Moreover, billions of dollars are spent prescribing anti-TNF therapies to patients that don't respond. There is a significant need for development of a technology that can identify responder vs non-responder subjects, prior to initiation of therapy, at the time that therapy (e.g., a particular dose) is administered, and/or over time as therapy has been or is received.

Gene expression data has been touted as holding the promise of being able to uncover disease biology of individual patients in complex diseases, but up until now the data has been difficult to interpret, and efforts to develop biomarkers (e.g., expression signatures) for therapeutic responsiveness have failed in cross-cohort validation tests. The present disclosure provides new technologies that, for example, consider relatively small changes in expression levels and/or participation of genes in relevant parts of the human interactome.

As already noted, the present disclosure demonstrates that projecting baseline gene expression profiles from UC patients that are non-responders to anti-TNF therapy on the HI, reveals that such profiles cluster and form a large connected module that describes the non-responders' disease biology. In accordance with the present invention, a classifier developed from genes expressed in this module predicts non-response with a high level of accuracy and has been validated in a completely independent cohort (cross-cohort validation). Furthermore, this classifier meets the commercial criteria set by insurance companies and is therefore ready for clinical development and future commercialization.

Methods

Microarray Analysis

Cohort 1, GSE14580: Twenty-four patients with active UC, refractory to corticosteroids and/or immunosuppression, underwent colonoscopy with biopsies from diseased colon within a week prior to the first intravenous infusion of 5 mg infliximab per kg body weight. Response to infliximab was defined as endoscopic and histologic healing at 4-6 weeks after first infliximab treatment using the MAYO score. Six control patients with normal colonoscopy were included. Total RNA was isolated from colonic mucosal biopsies, labelled and hybridized to Affymetrix™ Human Genome U133 Plus 2.0 Arrays.

Cohort 2, GSE12251: Twenty-two patients underwent colonoscopy with biopsy before infliximab treatment. Response to infliximab was defined as endoscopic and histologic healing at week 8 using the MAYO score (P2, 5, 9, 10, 14, 15, 16, 17, 24, 27, 36, and 45 as responders; P3, 12, 13, 19, 28, 29, 32, 33, 34, and 47 as non-responders). Messenger RNA was isolated from pre-infliximab biopsies, labeled and hybridized to Affymetrix™ HGU133 Plus 2.0 Array.

Identification of Classifier Genes

Genes with expression values across patients that were significantly correlated to clinical measures after treatment were selected as best determinants of response. These genes were mapped on the consolidated Human Interactome ("HI"). The consolidated Human Interactome collects physical protein interactions between a cell's molecular components relying on experimental support. The material reported by Barabási et al. in "Uncovering disease-disease relationships through the incomplete interactome," *Science*, 347 (6224):1257601 (February 2015), the entirety of which is incorporated herein by reference, provides instruction regarding how to build and curate a Human Interactome. The genes on the Human Interactome are not randomly scattered on the network. Instead, they significantly interact with each other, reflecting the existence of an underlying disease biology module that explains response.

Human Interactome

As noted, the HI contains experimentally supported physical interactions between cellular components. These interactions were queried from several resources but only selected those that are supported by experimental validation. Most of the interactions in the HI are from unbiased high-throughput studies such as Y2H. All included data were experimentally supported interactions that have been reported in at least two publications. These interactions include, regulatory, metabolic, signaling and binary interactions. The HI contains about 17k cellular components and over 200K interactions among them. Unlike other interaction databases, no computationally inferred interaction were included, nor any interaction curated from text parsing of literature with no experimental validation.

Classifier Design and Validation

Genes identified above were used as features of a probabilistic neural network. The classifier was validated using leave-one-out and/or k-fold cross validation within a given cohort. The classifier was trained based on the outcome data provided on all patients but the one left out. The classifier was blind to the response outcome of that left out patient. Predicting the outcome of the patient that has been left out then validated the trained classifier. This procedure was repeated so that each patient was left out once. The classifier provided a probability for each patient reflecting whether they belong to responder or non-responder group. The logarithm of likelihood ratio was used to assign a score to each patient. Patients were then ranked based on their score and prediction accuracy values were estimated by varying the classifier threshold resulting in the ROC curves. In particular, each patient is given a score by the trained classifier. The prediction accuracy is measured for the entire cohort as a whole and by checking whether given scores across patients well distinguish responders and non-responders. Prediction performance is generally measured by the Area Under the Curve (AUC). When higher levels of accuracy are required, negative predictive value (NPV) and true negative rate (TNR) can be used. The score cutoff that results in best group separation (e.g., highest NPV) is set for future predictions.

Example 2: Determining Responder and Non-Responder Patient Populations—Rheumatoid Arthritis Analogous to Example 1, the present Example 2 describes prediction of response and/or non-response to anti-TNF therapy in patients suffering from rheumatoid arthritis (RA). The presently described predictions satisfy the performance threshold identified by payers and physicians of Negative Predictive Value (NPV) of 0.9 and True Negative Rate (TNR) of 0.5.

In the present example, gene expression data from baseline blood samples for two cohorts comprising a total of 89 RA patients were analyzed. The methodology utilized in the present Example to develop a classifier (i.e., a gene expression response signature) that predicted response and/or non-response to anti-TNF therapy included a four step process. First, initial genes were selected based on differential expression between responders and non-responders to anti-TNF therapy. Second, such genes were projected on the human interactome to determine which genes form a significant and biologically relevant cluster. Third, genes that cluster on the interactome were selected and fed into a probabilistic neural network (PNN) to develop the final classifiers. And fourth, each classifier was validated using leave-one-out validation in the training set, and validated cross-cohort in an independent cohort of patients (test set). For RA, the final classifier contained 9 genes and reached an NPV of 0.91 and TNR of 0.67 in the test set.

The developed classifiers meet the performance thresholds set by payers and physicians; those skilled in the art will appreciate that these classifiers are useful tests that predict non-response to anti-TNFs prior to initiation of therapy and/or to assess desirability of altering administered therapy. Among other things, provided technology therefore permits selection of therapy (whether initial therapy or continued or altered therapy), including enabling patients to be switched onto alternative therapies faster, resulting in substantial clinical benefits to patients and savings to the healthcare system.

Data Description

The response prediction analysis in RA utilized in the present Example was based on two individual cohorts (Tables 3 and 4). Response was measured 14-weeks after initiation of anti-TNF therapy, with response rates (Good responders; DAS28 improvement>1.2, corresponding to LDA or remission) in cohort 1 and 2 of 30% and 23%, respectively. Cohort 1 was used to train the classifier and cohort 2 was used as the independent test cohort to validate the predictive power of the classifier.

The analyses were conducted on RNA expression data generated from whole blood, before initiation of therapy, using an Illumina™ BeadArray™ platform and provided as standard output of BeadStudio™. Raw data was normalized and processed using lumi package in R.

TABLE 3

| Clinical response according to EULAR DAS28 criteria | Cohort 1 | Cohort 2 |
|---|---|---|
| No. Good responders | 15 | 9 |
| No. Moderate responders | 15 | 15 |
| No. Non-responders | 20 | 15 |

TABLE 4

| | DAS28 Improvement | | |
|---|---|---|---|
| Baseline DAS28 | >1.2 | >0.6 & ≤1.2 | ≤0.6 |
| ≤3.2 | Good response | Moderate response | No response |
| >3.2 & ≤5.1 | Moderate response | Moderate response | No response |
| >5.1 | Moderate response | No response | No response |

Identifying Classifier Genes

Expression values for over 10,000 probes (genes) were available in each patient; those skilled in the art will appreciate the challenges associated with defining a set of genes (features) that effectively distinguishes response from such a volume of data. Insights provided by the present disclosure, including that particularly useful genes for inclusion in a classifier may, in some embodiments, be those with relatively small changes, permit effective selection of gene (feature) set(s) for use in a classifier.

In the present Example, genes for inclusion in an RA classifier were selected via a multi-step analysis: First, genes were ranked based on their significance of correlation to patient's response outcome (change in baseline DAS28 score at week 14) using Pearson correlation resulting in 200 top ranked genes (Feature set 1). Unlike conventional differential expression methods that look for highest fold changes in gene expression between two groups, the present Example captures small but significant changes between two groups of patients.

Figure 6:
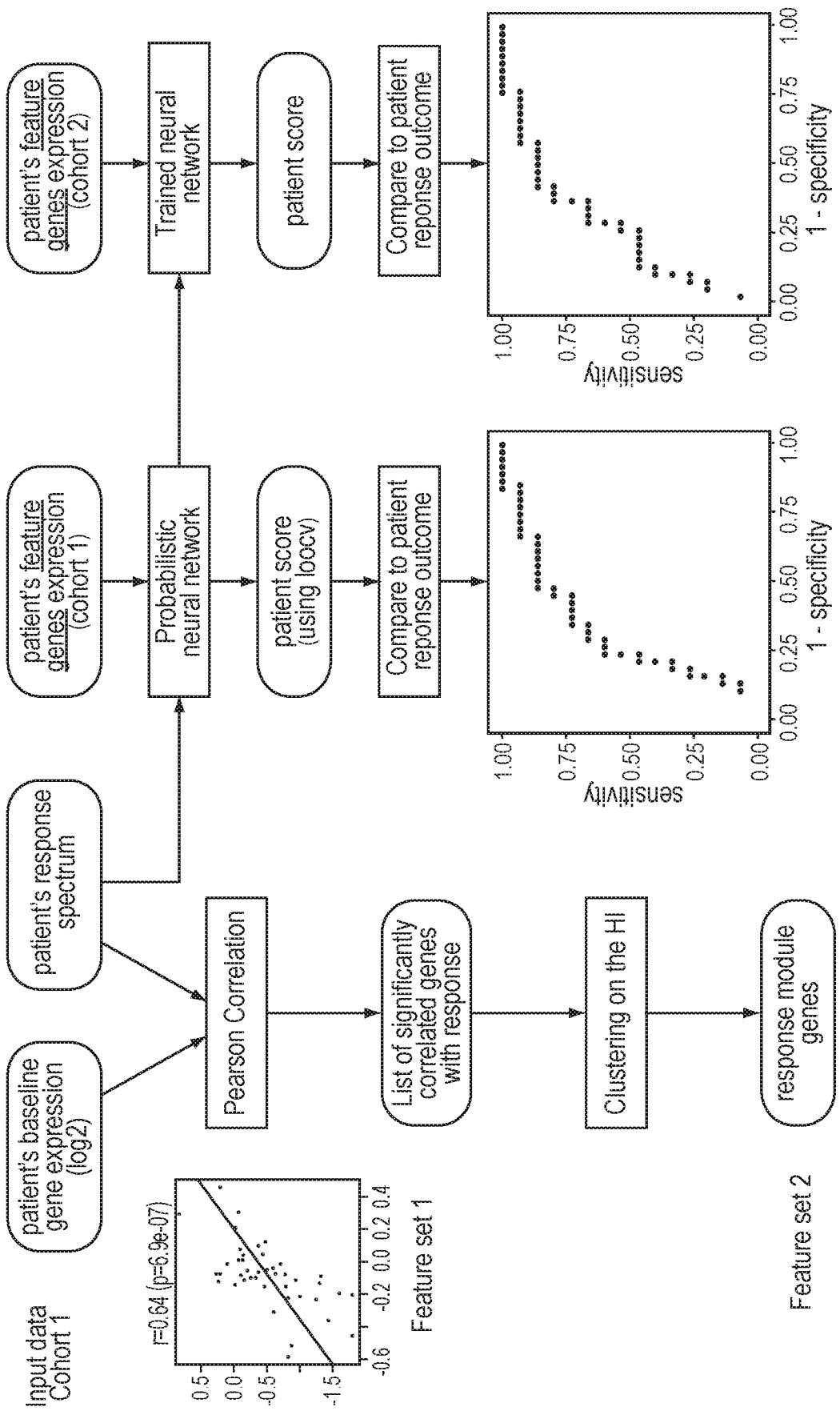
FIG. 6 is an exemplary workflow for developing a classifier.

Second, the present disclosure appreciates that gene products (proteins) do not function in isolation, and furthermore appreciates that reference to the interactome—a map of protein interconnectivity—can valuably be used as a blueprint to understand roles played by individual gene products in context (i.e., in biology of cells and/or organisms). By mapping the 200 genes identified above on the interactome, a significant cluster, or response module, consisting of 41 proteins was identified (Table 5). Existence of a significant cluster was repeatedly shown to be associated with underlying disease biology. The observed response module not only uncovers the underlying biology of response but also served as Features set 2. In particular, FIG. 6 illustrates a classifier development flowchart containing identifying features of the classifier (A), training and validation of a probabilistic neural network on cohort 1 using identified features (B) and validation of the trained classifier using identified feature genes expressions in an independent cohort (C). The final set of features are selected based on best performance.

TABLE 5

| Cohort ID | #Top genes selected | #Genes in HI | LCC size | Significance |
|---|---|---|---|---|
| 1 | 200 | 186 | 41 | 1.19 |

Training the Response Classifier and In-Cohort Validation

Figure 4A:
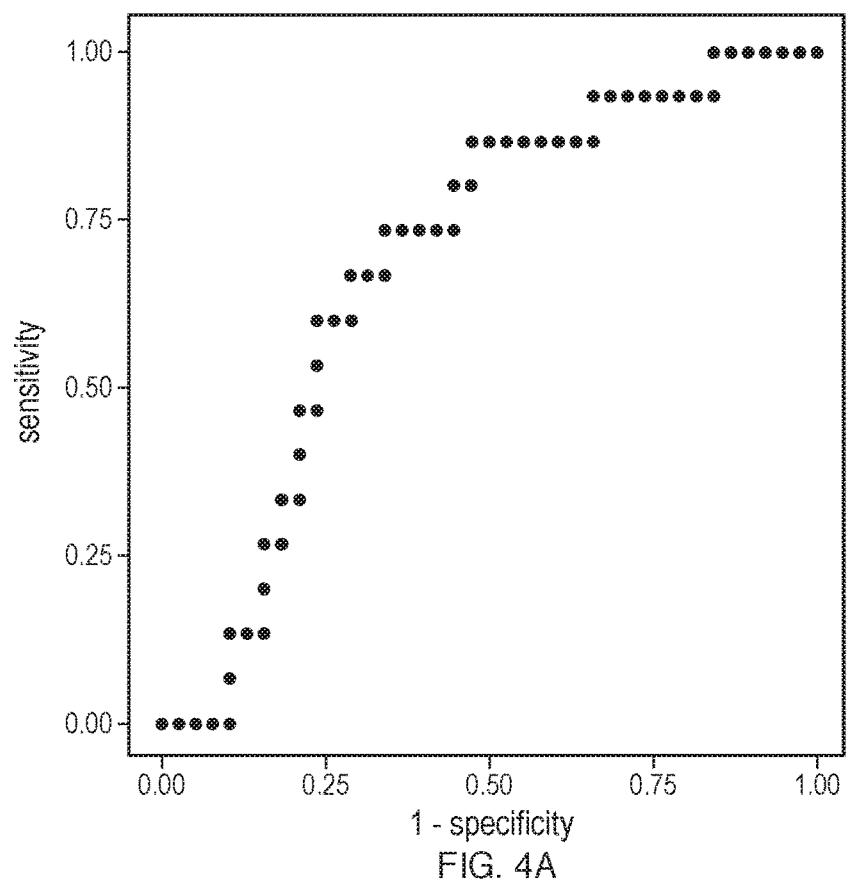
FIGS. 4A, 4B, 4C, and 4D are plots illustrating in-cohort rheumatoid arthritis (RA) classifier validation using leave-one-out cross validation when training on Feature Set 1 (FIGS. 4A and 4B) and top nine signature genes (FIGS. 4C and 4D).
Figure 4B:
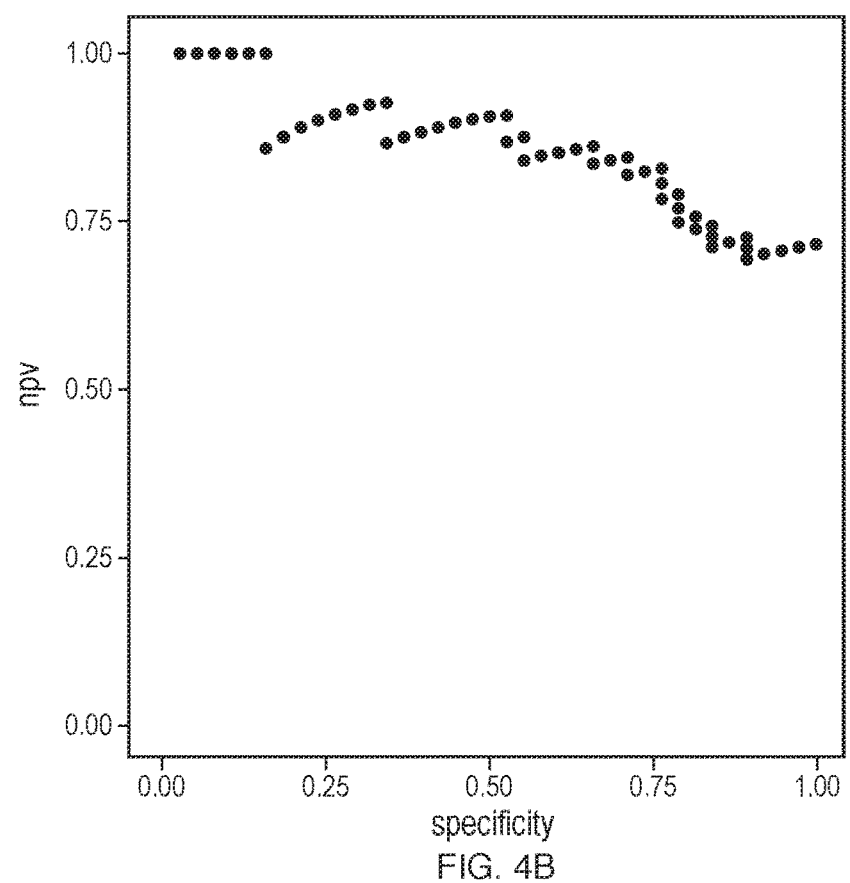
Figure 4C:
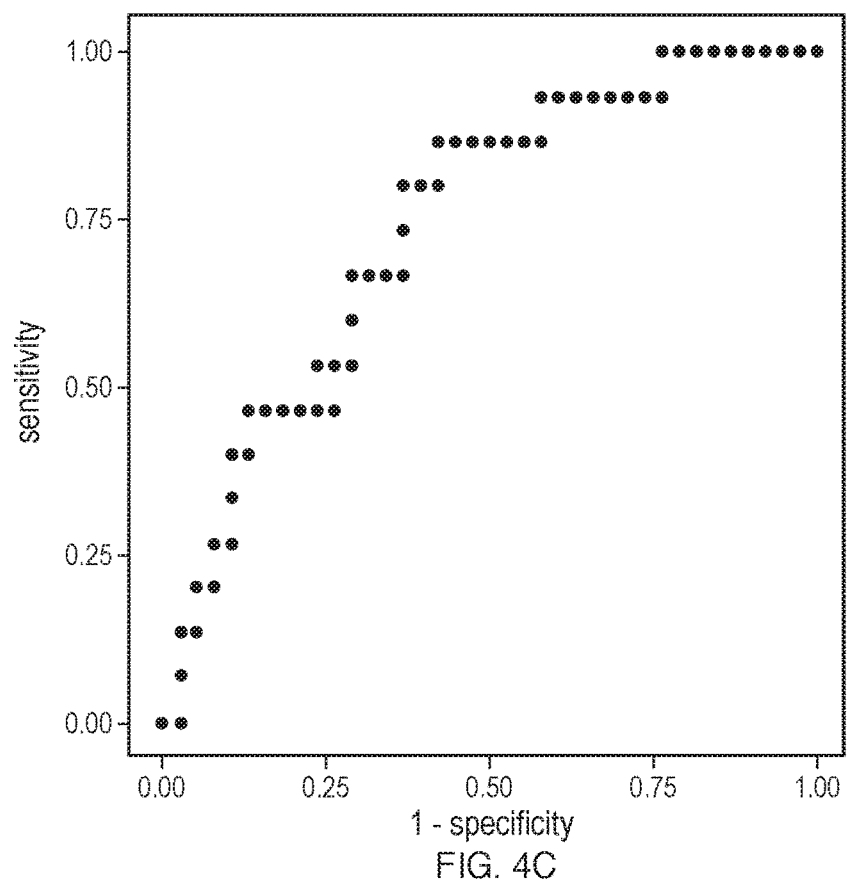
Figure 4D:
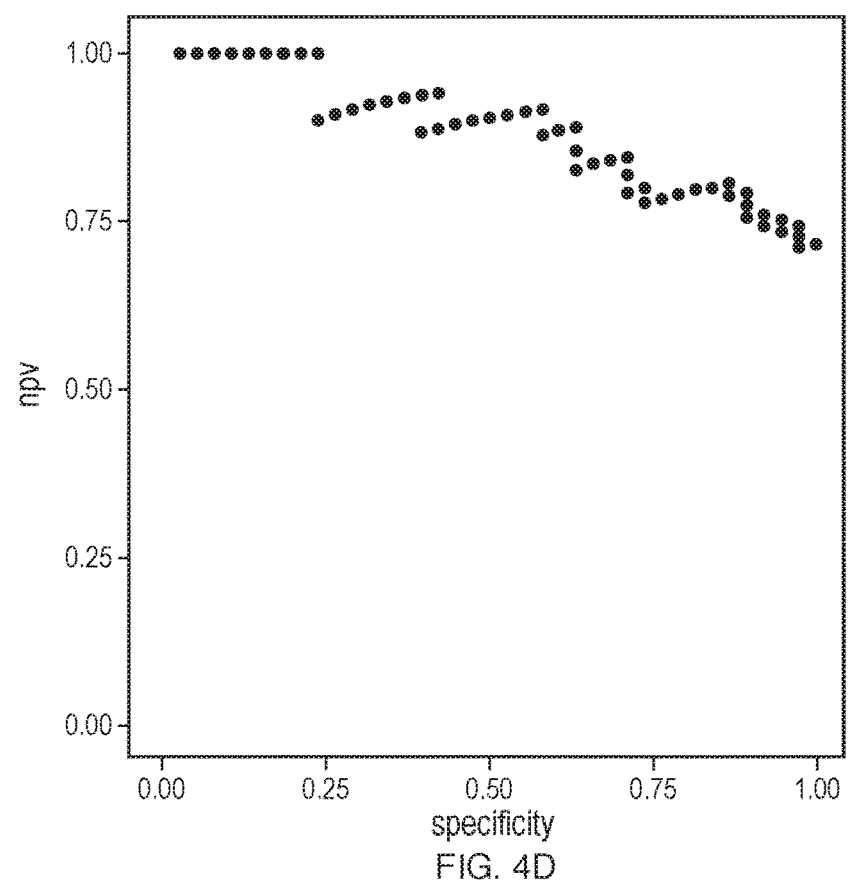

In the present Example, a response classifier was trained by feeding a probabilistic neural network with Feature set 1 and 2. Training the classifier on Feature set 1 significantly predicted response using leave-one-out cross validation and reached an AUC of 0.69, an NPV of 0.9 and a TNR of 0.52 (FIG. 4A, and FIG. 4B, respectively), outperforming Feature set 2. Having a smaller number of classifier genes also opens up the opportunity to use a variety of lower cost, FDA-approved expression platforms with a broad installed base to generate the required gene expression data sets. The classifier was therefore further trained to see if performance holds up when reducing the number of genes in Feature set 1 by training on top n-ranked genes where n goes from 1 to 20. A local maximum was observed in classifier performance when training on the top 9 genes (AUC=0.74, corrected p-value=0.006) with an NPV of 0.92 and a TNR of 0.76 (FIG. 4C and FIG. 4D). The 9-gene classifier was chosen for the cross cohort validation analysis below.

Validation of Trained Response Classifier in an Independent Cohort (Cross-Cohort Validation)

Figure 5A:
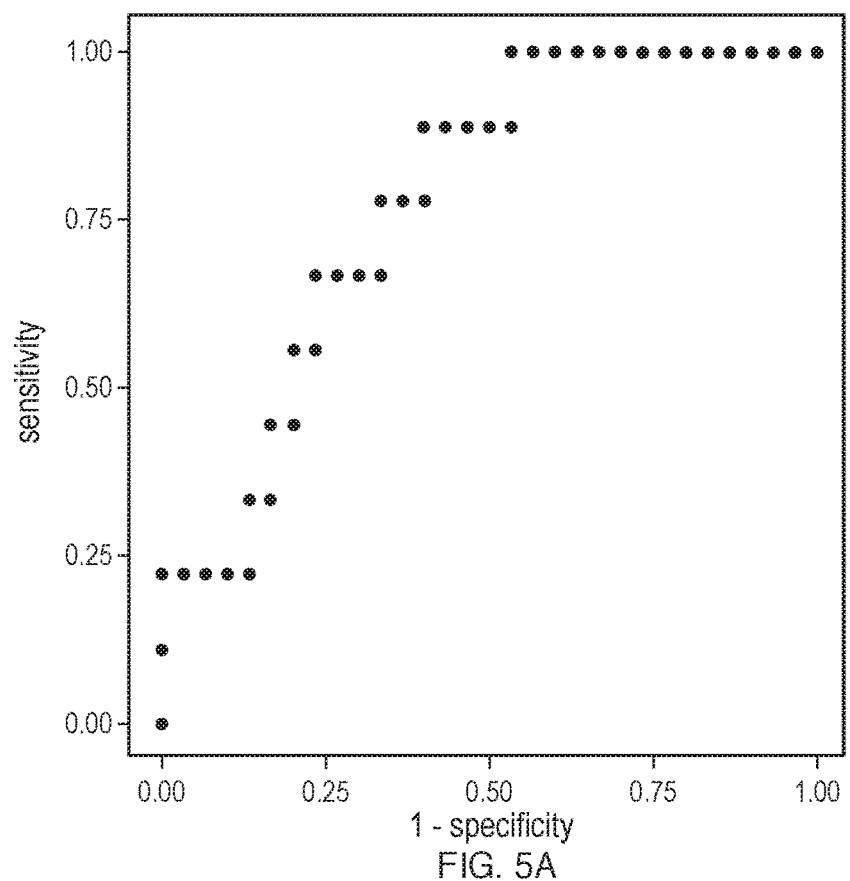
FIGS. 5A and 5B are plots illustrating ROC curves of cross cohort classifier test results (in FIG. 5A) and negative predictive performance (in FIG. 5B) for the RA classifier.
Figure 5B:
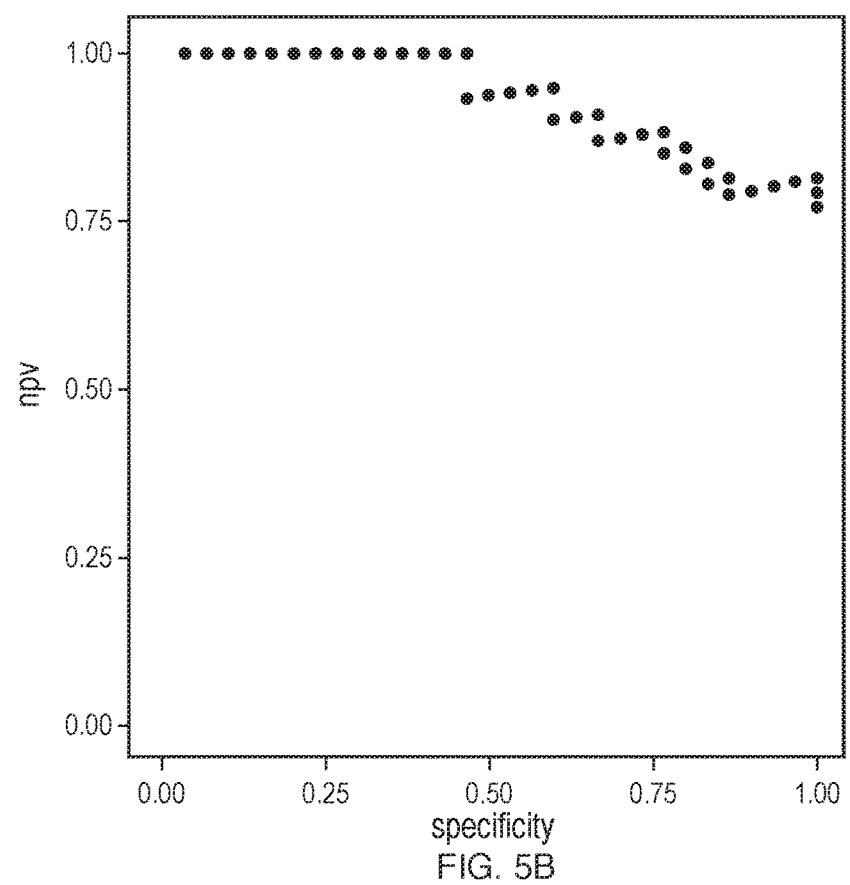

Of critical importance when building diagnostic tests and classifiers is the ability to reproduce the results and success-fully test the classifier's performance in an independent cohort. The developed 9-gene classifier was therefore tested in a blinded fashion on a completely independent group of patients (cohort 2). The results show that the classifier performed well (cross-cohort AUC=0.78, p value=0.01) with an NPV of 0.91 and a TNR of 0.67 (FIG. 5B and Table 6). FIG. 5A is an ROC curve of cross-cohort classifier test results.

TABLE 6

| Predicting non-responders for TNF-naïve patients | AUC | NPV | TNR |
|---|---|---|---|
| Classifier trained on cohort 1 tested on cohort 2 | 0.78 | 0.91 | 0.67 |

Discussion

The present Example documents effectiveness of a classifier, as described herein, that predicts non-response to anti-TNF drugs before therapy is prescribed in patients suffering from RA.

Interviews with payers and clinicians indicate that current target specifications aim to identify at least half of the non-responders to anti-TNF therapy with high negative predictive accuracy (NPV>90%). Patients that are identified as non-responders can be placed on alternative effective therapies and higher response rates for those patients still offered anti-TNFs can be achieved. Financial savings are garnered by not spending on expensive ineffectual therapies and avoiding serious side effects and continuing disease progression. By identifying 50% of the non-responders, significant cost and care benefits can be achieved since, in the absence of stratification, two-thirds of patients do not achieve the target of LDA or remission today. High NPV is desired to ensure that few patients that would have responded are not incorrectly withheld a therapy they would have benefited from.

For RA, the present disclosure has demonstrated an AUC of 0.78, an NPV of 0.91 and a TNR of 0.67, resulting in the matrix below (Table 7). That is, the classifier identifies 67% of true non-responders with a 91% accuracy. Stratifying patients using this classifier would increase the response rate for the anti-TNF treated group by 71% from 34% to 58%. By comparison, the highest cross-cohort performance reported for classifiers developed by others had an NPV of 0.71 and a TNR of 0.71. See Toonen E J. et al. "Validation study of existing gene expression signatures for anti-TNF treatment in patients with rheumatoid arthritis." *PLoS One.* 2012; 7(3):e33199. Using that classifier would significantly misclassify the genuine responders leading to a worse overall response rate than not using it at all. The presently described classifiers clearly meet the performance targets when tested in an independent cohort of patients.

TABLE 7

| | | Predicted | | | |
|---|---|---|---|---|---|
| | | R | NR | | |
| Actual | R | 30 | 4 | 34 | TPR 87% |
| | NR | 22 | 44 | 66 | TNR 67% |
| | | 52 | 48 | | |
| | | PPV 58% | NPV 91% | | |

The reduced number of genes in the classifier allows several expression analysis platforms to be considered for the delivery of the final commercial version of the test. For example, Nanostring nCounter system uses digital barcode technology to count nucleic acid analytes for panels of up to several hundred genes on an FDA approved platform. Multiplexed qRT-PCR is the gold standard for quantifying gene expression for panels of less than ~20 genes and would enable the test to be offered as a distributable kit. RA is a chronic, complex autoimmune diseases, where many genetic risk factors have been identified but none of them are of sufficient impact to be useful as diagnostic or prognostic markers. The present disclosure provides a ranked list of candidate genes based on correlation of baseline expression level with response outcomes. The rank order is derived from the significance of the correlation. The present disclosure, however, does not prioritize genes with larger fold change across the category of responders and non-responders. It is common practice in the field to give preference to genes that show the highest fold change. This is because it is generally believed that large changes in expression levels are biologically more meaningful, and because of the technical advantage of high signal to noise ratios to compensate for high background and other sources of technical variability. However, the present disclosure appreciates that small differences, which are ignored or overlooked in many conventional technologies, can provide important, and even critical, discriminating capability. Without wishing to be bound by any particular theory, the present disclosure proposes that subtle differential perturbations may be particularly relevant and/or important in situations, like the present, where subjects suffering from the same disease, disorder, or condition are compared with one another (e.g., rather than with "control" subjects not suffering from the disease, disorder, or condition). It may be that small yet statistically significant differences in gene expression differentiate patient populations in complex diseases such as RA. This study shows that even very small but significant changes in gene expression will lead to a different treatment outcome. This method captures genes that are overlooked by conventional differential expression analysis.

Additionally, the present disclosure utilizes the highly unbiased and independently validated map of the protein-protein interactions in cells, the human interactome. By mapping the prioritized genes to the interactome, distinct and statistically significant clusters appear. In addition to using the interactome network analysis to define the classifier, the identified clusters also provide biological insights into the biology and causal genes of anti-TNF response. The genes corresponding to the top 9 genes in RA are valuable in immunological pathways and functions linked to ER stress, the protein quality control pathway, control of the cell cycle and the ubiquitin proteasome system, primarily in targeting key regulators of the cell cycle to the proteasome through ubiquitinyation.

The classifiers described here serve as the basis for diagnostic tests to predict anti-TNF non-response for patients with moderate to severe disease and considering initiating biologic therapy. Patients identified as non-responders will be offered alternative, approved mechanism of action therapies. These tests will provide significant improvements to current clinical practice by increasing the proportion of patients reaching treatment goals, making the treatment assignment based on scientific data and as a result decrease waste of resources and generate significant financial savings within the health care system.

Materials and Methods

RA Cohort Description and Microarray Analysis

Blood samples were collected from RA patients across the United States from two individual observational studies, both of which predominantly consisted of older Caucasian women. Cohort 1 was obtained from a multi-center study conducted in 2014. These patients were treated with Enbrel, Remicade, Humira, Cimzia and Simponi. Cohort 2 was obtained from the Autoimmune Biomarkers Collaborative Network, a NIAMS supported contract to develop new approaches to biomarkers for RA and lupus in 2003. These patients were treated with Humira, Remicade and Enbrel.

The level of response was defined using the EULAR DAS28 scoring criteria assessed 14 weeks after anti-TNF treatment. EULAR response rates for female TNF naïve patients are given in Table 1. EULAR response characterizes patients into good responders, moderate responders and non-responders. For this study, response was defined as EULAR good response, or DAS28 improvement>1.2. This corresponds to LDA or remission.

The gene expression data and 14 week response outcome was available for 50 and 39 female and TNF naïve samples in cohort 1 and 2, respectively, for classifier design and validation.

All subjects had PaxGene® tubes drawn at baseline before starting therapy, and again at 14 weeks after treatment started. RNA was isolated using the QIAcube® (Qiagen®) following the manufacturer's automated protocol for PaxGene® blood RNA. Extracted samples were eluted in 80 ul of elution buffer (BR5) and subsequently run on Agilent's 2100 Bioanalyzer™ of RNA integrity using the RNA 6000 Nanochip. Samples with RNA Integrity Numbers (RIN) >6.5 were diluted to 30 ng/µl in a total 11 µl of RNAse-free water. Samples were amplified using Life Technologies Illumina™ RNA Total Prep™ Amplification Kit. 750 ng of cRNA was re-suspended in 5 µl of RNAse-free water for analysis on the Illumina™ Human HT-1.2v4 chip (cohort 1 samples) and 1.2 µg was re-suspended in 10 µl of RNAse-free water for analysis Illumina™ WG6v3 Bead Chip (cohort 2 samples). All samples were processed according to the manufacturer's instructions.

Raw data were exported from GenomeStudio™ and further analyzed with the R programming language. All datasets were background corrected using the R/Bioconductor package "lumi." Data were further transformed using variance stabilization transformational (vst) and quantile normalized. Probes with zero detection count and detection rates of lower that 50% across samples were removed from the study. To enable cross cohort classifier testing, the two cohorts were combined and normalized using the ComBat package in R and then separated to ensure completely blind testing. All of the microarray analysis resulted in having about 10,000 common probes in the two cohorts.

Identification of Classifier Genes

Genes with expression values that are significantly correlated to clinical measures after treatment are selected as the best determinants of response. Expression correlation of gene expression to response outcome is measured by Pearson correlation. Genes are ranked based on the correlation value and the performance of the classifier is assessed when using top n ranked genes. In some cases mapping the ranked genes on the interactome forms a significant cluster reflecting the underlying biology of response. It is observed that the ranked genes are not randomly scattered on the network. Instead, they significantly interact with each other, reflecting the existence of an underlying disease biology module that explains response.

Classifier Design and Validation

Genes identified in the previous step were used as features of a probabilistic neural network. In this approach the average distance of each sample to training samples' probability distribution functions is calculated. The average distance of a test sample to training samples in the n-dimensional feature space determines the probability of belonging to one group vs. the other. The classifier was validated using leave-one-out cross validation within a given cohort. In this approach, the classifier was trained based on the outcome data provided on all patients but the one left out. The classifier was blind to the response outcome of that left out patient. Predicting the outcome of the patient that has been left out then validated the trained classifier. This procedure was repeated so that each patient was left out once. The classifier provided a probability for each patient reflecting whether they responded or not. These probabilities were used to define a score (by using log of likelihood ratio) for each patient. The area under the curve (AUC) determined the performance of the classifier. In cross-cohort assessment of the classifier, the trained classifier was completely blind to the outcome of the independent cohort. Trained data on one cohort is tested to determine its ability to predict response in an independent cohort.

Statistical Analysis

Fisher's t-test was used to determine the significance of difference between two distributions.

Human Interactome

The human interactome contains experimentally supported physical interactions between cellular components. These interactions are collected from several resources but only those supported by a rigorous experimental validation confirming the existence of a physical interaction between proteins are selected. Most of the interactions in the interactome are from unbiased high-throughput studies such as yeast 2-hybrid. Experimentally supported interactions that that have been reported in at least two publications are also included. These interactions include regulatory, metabolic, signaling and binary interactions. The interactome contains about 17,000 cellular components and over 200,000 interactions. Unlike other interaction databases the present methods do not include any computationally inferred interactions, nor any interaction curated from text parsing of literature with no experimental validation. Therefore, the interactome used is the most complete, carefully selected and quality controlled version to date.

The foregoing has been a description of certain non-limiting embodiments of the subject matter described within. Accordingly, it is to be understood that the embodiments described in this specification are merely illustrative of the subject matter reported within. Reference to details of the illustrated embodiments is not intended to limit the scope of the claims, which themselves recite those features regarded as essential.

It is contemplated that systems and methods of the claimed subject matter encompass variations and adaptations developed using information from the embodiments described within. Adaptation, modification, or both, of the systems and methods described within may be performed by those of ordinary skill in the relevant art.

Throughout the description, where systems are described as having, including, or comprising specific components, or where methods are described as having, including, or comprising specific steps, it is contemplated that, additionally, there are systems encompassed by the present subject matter that consist essentially of, or consist of, the recited components, and that there are methods encompassed by the present subject matter that consist essentially of, or consist of, the recited processing steps.

It should be understood that the order of steps or order for performing certain action is immaterial so long as any embodiment of the subject matter described within remains operable. Moreover, two or more steps or actions may be conducted simultaneously.

The invention claimed is:

1. A method of treating subjects suffering from an autoimmune disease, disorder or condition with anti-TNF therapy, the method comprising a step of:
    administering the anti-TNF therapy to subjects who have been assessed to lack a validated gene expression response signature indicative of non-response to anti-TNF therapy,
    wherein the absence of the validated gene expression response signature has been determined by a validated classifier, wherein said validated classifier has been obtained by:
        analyzing gene expression levels in biological samples from a first cohort of subjects who have previously received the anti-TNF therapy ("prior subjects") and have been determined to respond ("responders") or not to respond ("non-responders") to the anti-TNF therapy to identify genes that show statistically significant differences in expression level between the responders and the non-responders ("signature genes")
        mapping the signature genes onto a human interactome and selecting a subset of the signature genes that map onto a connected module of the human interactome ("candidate gene list");
        training a classifier on expression levels of the genes of the candidate gene list from the first cohort of subjects to identify a subset of the prior subjects having a pattern of expression of the candidate gene list indicative that the subset of prior subjects are unlikely to respond to the anti-TNF therapy, to thereby obtain a trained classifier; and
        obtaining the validated classifier by validating the trained classifier on a second cohort comprising an independent and blinded group of responders and non-responders and selecting a cutoff score such that the validated classifier predicts non-responders with a true negative rate (TNR) of at least 0.5 and a negative predictive value (NPV) of at least 0.9, wherein subjects falling within the group of predicted non-responders display the validated gene expression response signature and subjects that do not fall within the group of predicted non-responders lack the validated gene expression response signature; and
    wherein the anti-TNF therapy is an antibody or a decoy circulating receptor fusion protein.

2. The method of claim 1, wherein each of the prior subjects suffered from the same autoimmune disease, disorder, or condition.

3. The method of claim 2, wherein the subjects to whom the anti-TNF therapy is administered are suffering from the same autoimmune disease, disorder or condition as the prior subjects.

4. The method of claim 1, wherein the candidate gene list is selected from a cluster of genes associated with non-response to anti-TNF therapy on a human interactome map.

5. The method of claim 1, wherein the anti-TNF therapy is or comprises administration of infliximab, adalimumab, etanercept, cirtolizumab pegol, golimumab, or biosimilars thereof.

6. The method of claim 5, wherein the anti-TNF therapy is or comprises administration of infliximab or adalimumab.

7. The method of claim 1, wherein the autoimmune disease, disorder, or condition is selected from rheumatoid arthritis, psoriatic arthritis, ankylosing spondylitis, Crohn's disease, ulcerative colitis, chronic psoriasis, hidradenitis suppurativa, and juvenile idiopathic arthritis.

8. The method of claim 1, further comprising:
   determining, prior to the administering, lacks a validated gene expression response signature indicative of non-response to anti-TNF therapy.

9. The method of claim 8, wherein the step of determining comprises measuring gene expression by at least one of a microarray, RNA sequencing, real-time quantitative reverse transcription PCR (qRT-PCR), bead array, and ELISA.

10. The method of claim 1, wherein the second cohort comprises at least 39 combined responders and non-responders.

11. The method of claim 1, wherein the validated classifier predicts non-responders with a true negative rate (TNR) of at least 0.65.

* * * * *

UNITED STATES PATENT AND TRADEMARK OFFICE
CERTIFICATE OF CORRECTION

| | |
|---|---|
| PATENT NO. | : 11,198,727 B2 |
| APPLICATION NO. | : 16/394046 |
| DATED | : December 14, 2021 |
| INVENTOR(S) | : Susan Ghiassian et al. |

It is certified that error appears in the above-identified patent and that said Letters Patent is hereby corrected as shown below:

On the Title Page

Item (72) Inventors:
Please replace:
"Susan Dina Ghiassian"
With:
"Susan Ghiassian"

Signed and Sealed this
Eighth Day of August, 2023

Katherine Kelly Vidal
*Director of the United States Patent and Trademark Office*